US008501440B2

(12) United States Patent
Weiss

(10) Patent No.: US 8,501,440 B2
(45) Date of Patent: *Aug. 6, 2013

(54) FIBRILLATION-RESISTANT INSULIN AND INSULIN ANALOGUES

(75) Inventor: Michael Weiss, Moreland Hills, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/472,833

(22) Filed: May 16, 2012

(65) Prior Publication Data

US 2012/0316107 A1 Dec. 13, 2012

Related U.S. Application Data

(63) Continuation of application No. 12/419,169, filed on Apr. 6, 2009, now Pat. No. 8,192,957, which is a continuation-in-part of application No. PCT/US2007/080467, filed on Oct. 4, 2007.

(60) Provisional application No. 60/828,153, filed on Oct. 4, 2006.

(51) Int. Cl.
*A61K 38/28* (2006.01)
*C07K 14/62* (2006.01)
*C12N 15/17* (2006.01)
*C12N 15/63* (2006.01)

(52) U.S. Cl.
USPC ..... 435/69.7; 435/69.1; 435/71.1; 435/320.1; 514/6.2; 514/6.3; 530/303

(58) Field of Classification Search
None
See application file for complete search history.

(56) References Cited

U.S. PATENT DOCUMENTS

| | | | |
|---|---|---|---|
| 5,149,716 A | 9/1992 | Vertesy et al. | |
| 5,149,777 A | 9/1992 | Hansen et al. | |
| 5,491,216 A | 2/1996 | Hoffmann et al. | |
| 5,506,202 A | 4/1996 | Vertesy et al. | |
| 5,618,913 A | 4/1997 | Brange et al. | |
| 5,698,669 A | 12/1997 | Hoffmann et al. | |
| 5,700,662 A | 12/1997 | Chance et al. | |
| 5,716,927 A | 2/1998 | Balschmidt et al. | |
| 5,977,297 A | 11/1999 | Obermeier et al. | |
| 6,011,007 A | 1/2000 | Havelund et al. | |
| 6,221,633 B1 | 4/2001 | Ertl et al. | |
| 6,268,335 B1 | 7/2001 | Brader | |
| 6,465,426 B2 | 10/2002 | Brader | |
| 6,531,448 B1 | 3/2003 | Brader | |
| 6,630,348 B1 | 10/2003 | Lee et al. | |
| 7,129,211 B2 | 10/2006 | Bhattacharya et al. | |
| 7,316,999 B2 | 1/2008 | Hoeg-Jensen et al. | |
| 7,547,821 B2 | 6/2009 | Moloney et al. | |
| 8,192,957 B2 * | 6/2012 | Weiss ........................... | 435/69.7 |
| 2001/0036916 A1 | 11/2001 | Brader | |
| 2002/0082199 A1 | 6/2002 | Brader | |
| 2003/0104981 A1 | 6/2003 | Mandic | |
| 2003/0144181 A1 | 7/2003 | Brader | |
| 2004/0014660 A1 | 1/2004 | During et al. | |
| 2004/0053816 A1 | 3/2004 | Bhattacharya et al. | |
| 2004/0214988 A1 | 10/2004 | Tirrell et al. | |
| 2005/0014679 A1 | 1/2005 | Beals et al. | |
| 2005/0039235 A1 | 2/2005 | Moloney et al. | |
| 2005/0176621 A1 | 8/2005 | Brader et al. | |
| 2006/0217290 A1 | 9/2006 | Kohn et al. | |
| 2007/0129284 A1 | 6/2007 | Kjeldsen et al. | |
| 2008/0146492 A1 | 6/2008 | Zimmerman et al. | |
| 2009/0304814 A1 | 12/2009 | Weiss | |
| 2011/0059887 A1 | 3/2011 | Weiss | |
| 2011/0077196 A1 | 3/2011 | Weiss | |
| 2011/0077197 A1 | 3/2011 | Habermann et al. | |
| 2011/0166064 A1 | 7/2011 | Weiss | |
| 2011/0103575 A1 | 8/2011 | Weiss | |
| 2011/0195896 A1 | 8/2011 | Weiss et al. | |

FOREIGN PATENT DOCUMENTS

| | | |
|---|---|---|
| EP | 1 090 640 A2 | 4/2001 |
| WO | 03053339 A2 | 7/2003 |
| WO | 2005054291 A1 | 6/2005 |
| WO | 2007081824 A2 | 7/2007 |
| WO | 2007096332 A1 | 8/2007 |
| WO | 2007081824 A3 | 2/2008 |
| WO | 2008043033 A2 | 4/2008 |
| WO | 2008043033 A3 | 11/2008 |

(Continued)

OTHER PUBLICATIONS

EP 07 84 3856 Supplementary European Search Report dated Dec. 11, 2009.
EP 09 80 3678 Supplementary European Search Report dated Jan. 30, 2012.
PCT/US2007/080467 International Search Report and Written Opinion dated Sep. 16, 2008.
PCT/US2010/047546 International Search Report and Written Opinion dated May 23, 2011.
PCT/US2010/060085 International Search Report and Written Opinion dated Sep. 16, 2011.

(Continued)

*Primary Examiner* — Christine J Saoud
(74) *Attorney, Agent, or Firm* — Hahn Loeser & Parks LLP; John J. Cunniff

(57) ABSTRACT

A fibrillation-resistant insulin analogue may be a single-chain insulin analogue or a physiologically acceptable salt thereof, containing an insulin A chain sequence or an analogue thereof and an insulin B chain sequence or an analogue thereof connected by a polypeptide of 4-10 amino acids. The fibrillation-resistant insulin analogue preferably displays less than 1 percent fibrillation with incubation at 37° C. for at least 21 days. A single-chain insulin analogue displays greater in vitro insulin receptor binding than normal insulin while displaying less than or equal binding to IGFR than normal insulin. The fibrillation-resistant insulin may be used to treat a patient using an implantable or external insulin pump, due to its greater fibrillation resistance.

18 Claims, 9 Drawing Sheets

FOREIGN PATENT DOCUMENTS

| | | |
|---|---|---|
| WO | 2009087081 A2 | 7/2009 |
| WO | 2009129250 A2 | 10/2009 |
| WO | 2009132129 A2 | 10/2009 |
| WO | 2009132129 A3 | 1/2010 |
| WO | 2009129250 A3 | 2/2010 |
| WO | 2010014946 A2 | 2/2010 |
| WO | 2010014946 A3 | 5/2010 |
| WO | 2011028813 A2 | 3/2011 |
| WO | 2011072288 A2 | 6/2011 |
| WO | 2011103575 A1 | 8/2011 |

OTHER PUBLICATIONS

PCT/US11/25730 International Search Report and Written Opinion dated Jul. 22, 2011.

Blanquart et al.; Characterization of IRA/IR hybrid insulin receptors using bioluminescence resonance energy transfer; Biochemical Pharmacology 76 (2008); Jul. 27, 2008, pp. 873-883.

Chen et al.; Sequences of B-Chain/Domain 1-10/1-9 of Insulin and Insulin-like Growth Factor 1 Determine Their Different Folding Behavior; Biochemistry; pp. 9225-9233; 2004.

Currie et al.; The influence of glucose-lowering therapies on cancer risk in type 2 diabetes; Diabetologia; 52(9); pp. 1766-1777; Sep. 2009.

Doig et al.; N- and C-capping preferences for all 20 amino acids in {alpha}-helical peptides; Protein Science; vol. 4; pp. 1325-1335; 1995.

Du et al.; Insulin analogs with B24 or B25 phenylalanine replaced by biphenylalanine; Acta Biochem Biophys Sin; vol. 40, No. 2; pp. 133-139; Feb. 2008.

Duckworth et al.; Degradation products of insulin generated by hepatocytes and by insulin protease; Journal of Biological Chemistry, vol. 263, No. 4, Apr. 6, 1988; pp. 1826-1833.

Garriques et al.; The effect of mutations on the structure of insulin fibrils studied by Fourier transform infrared (FTIR) spectroscopy and electron microscopy; PubMed; vol. 12; 1 page (abstract only); 2002.

Haijuan Du et al.; Insulin analogs with B24 or B25 phenylalanine replaced by bipheylalanine; ACTA Biochimica et Biophysica Sinica, vol. 40, No. 2, 2006, pp. 133-139.

Hemkens et al.; Risk of malignancies in patients with diabetes treated with human insulin or insulin analogues: a cohort study; Diabetologia 52(9); pp. 1732-1744; Sep. 2009.

Hua et al.; Design of an Active Ultrastable Single-chain Insulin Analog; The Journal of Biological Chemistry; vol. 283, No. 21; pp. 14703-14716; May 23, 2008.

Hua et al.; Mechanism of insulin fibrillation—The structure of insulin under amyloidogenic conditions resembles a protein-folding intermediate, Journal of Biological Chemistry; vol. 279, No. 20; pp. 21449-21460, XP002557730, ISSN 0021-9258; May 14, 2004.

Huang et al.; Structure-Specific Effects of Protein Topology on Cross-β Assembly: Studies of Insulin Fibrillation; Biochemistry 2006, 45, pp. 10278-10293, Aug. 24, 2006.

Kaarsholm et al.; Engineering Stability of the Insulin Monomer Fold with Application Structure-Activity Relationships; Biochemistry; 32 (40); pp. 10773-10778, Oct. 1993.

Kohn et al.; pI-shifted insulin analogs with extended in vivo time action and favorable receptor selectivity; Peptides; 28 (4); Jan. 25, 2007; pp. 935-948.

Kohn et al.; pI-shifted insulin analogs with extended in vivo time action and favorable receptor selectivity; PubMed; 28 (4); 1 page (abstract only); Jan. 25, 2007.

Kristensen et al.; Alanine Scanning Mutagenesis of Insulin; The Journal of Biological Chemistry; vol. 272, No. 20; pp. 12978-12983, May 16, 1997.

Liefvendahl et al.; Mitogenic effect of the insulin analogue glargine in malignant cells in comparison with insulin and IGF-I; PubMed; 1 page (abstract only); Apr. 7, 2008.

Liu et al.; Utilization of combined chemical modification to enhance the blood-brain barrier permeability and pharmacological activity of endomorphin-a, JPET 106, 106484, Jun. 27, 2006, pp. 1-43.

Mayer et al.; Proliferative effects of insulin analogues on mammary epithelial cells; Archives of Physiology and Biochemistry; 114(1); pp. 38-44; Feb. 2008.

Milazzo et al.; ASPB10 insulin induction of increased mitogenic responses and phenotypic changes in human breast epithelial cells; evidence for enhanced interations with the insulin-like growth factor-I receptor; PubMed; 18(1); 1 page (abstract only); Jan. 1997.

Mirmira et al.; Disposition of the phenylalanine B25 side chain during insulin-receptor and insulin-insulin interactions, Biochemistry; vol. 30, No. 33; May 1, 1991, pp. 8222-8229.

Mirmira et al.; Importance of the character and configuration of residues B24 B25 and B26 in insulin-receptor interactions, Journal of Biological Chemistry, vol. 266, No. 3; Jan. 25, 1991; pp. 1428-1436.

Mirmira et al.; Role of the Phenylalanine B24 Side Chain in Directing Insulin Interaction with Its Receptor; The Journal of Biological Chemistry; vol. 264, No. 11; pp. 6349-6354; Apr. 15, 1989.

Nakagawa, et al.; Chiral Mutagenesis of Insulin; The Journal of Biological Chemistry; vol. 281, No. 31; pp. 22386-22396; Aug. 4, 2006.

Nielsen et al.; Probing the Mechanism of Insulin Fibril Formation with Insulin Mutants; American Chemical Society; Biochemistry; vol. 40; pp. 8397-8409; Jun. 19, 2001.

Olsen et al.; The Relationship Between Insulin Bioactivity and Structure in the NH2-terminal A-chain Helix; Journal of Molecular Biology; vol. 284, Issue 2, pp. 477-488, Nov. 27, 1998.

Rajpal et al.; Single-Chain Insulins as Receptor Agonists; The Endrocrine Society; 27 pages; Feb. 19, 2009.

Shukla et al.; Analysis of signaling pathways related to cell proliferation stimulated by insulin analogs in human mammary epithelial cell lines; Endrocine-Related Cancer; 16(2); pp. 429-441; Jun. 2009.

Sleiker et al.; Modifications in the B10 and B26-30 regions of the B chain of human insulin alter affinity for the human IGF-I receptor more than for the insulin receptor; Diabetologia; 40 Suppl. 2; Jul. 1997; pp. S54-S61.

Sreekanth et al.; Structural interpretation of reduced insulin activity as seen in crystal structure of human Arg-insulin; Biochimie; 90(3); Sep. 22, 2007; pp. 467-473.

Stemaszynska et al.; N-(2-Oxoacyl)amino Acids and Nitriles as Final Products of Dipeptide Chlorination Mediated by the Myeloperoxidase/H2O2/CI-System, European Journal of Biochemistry, vol. 92, No. 1, Sep. 25, 1978, pp. 301-308.

Summ et al.; Binding of insulin analogs to partially purified insulin receptor from rat liver membrane (author's trans.); Hoppe Seylers Z. Physiol. Chem.; 357(5); May 1976; pp. 683-693 (Abstract only—1 page).

Tuffs; German agency suspects that insulin analogue glargine increases risk of cancer; PubMed; BMJ; 339:b2774; 1 page (no abstract available); Jul. 8, 2009.

Wan et al.; Enhancing the Activity of Insulin at the Receptor Interface: Crystal Structure and Photo-Cross-Linking of A8 Analogues; Biochemistry 2004, 43; Nov. 25, 2004; pp. 16119-16133.

Weinstein, et al.; Insulin analogues display IGF-I-like mitogenic and anti-apoptotic activities in cultured cancer cells; Diabetes/Metabolism Research and Reviews; 25(1); pp. 41-49; Jan. 2009.

Weiss, et al.; Activities of Monomeric Insulin Analogs at Position A8 Are Uncorrelated with Their Thermodynamic Stabilities; The Journal of Biological Chemistry; vol. 276, No. 43; pp. 40018-40024; Oct. 26, 2001.

Weiss et al.; Non-standard Insulin Design: Structure-Activity Relationships at the Periphery of the Insulin Receptor; The Journal of Molecular Biology; vol. 315; pp. 103-111, 2002.

Yang et al.; An Achilles' heel in an amyloidogenic protein and its repair: insulin fibrillation and therapeuric design; J. Biol Chem. Apr. 1, 2010:285(14):10806-21, Apr. 2, 2010.

Zakova et al.; Shortened Insulin Analyogues: Marked Changes in Biological Activity Resulting from Replacement of TyrB26 and N-Methylation of Piptide Bonds in the C-Terminus of the B-Chain; Biochemistry; vol. 43; pp. 2323-2331; 2004.

Zelobowska et al.; Mitogenic potency of insulin glargine; Polish Journal of Endocrinology; vol. 60, No. 1; pp. 34-39; 2009.

Zhao et al.; Design of an insulin analog with enhanced receptor binding selectivity: rationale, structure, and therapeutic implications; J. Biol. Chem. 284(46); Sep. 22, 2009; pp. 32178-32187.

\* cited by examiner

PROINSULIN

MODEL

FIBRILLATION-RESISTANT INSULIN AND INSULIN ANALOGUES

CROSS REFERENCE TO RELATED APPLICATIONS

This application is a continuation of co-pending U.S. patent application Ser. No. 12/419,169 filed Apr. 6, 2009, which is a continuation-in-part of co-pending International Application No. PCT/US07/80467 filed Oct. 4, 2007, which in turn claims priority from U.S. Provisional Application No. 60/828,153 filed on Oct. 4, 2006.

STATEMENT REGARDING FEDERALLY SPONSORED RESEARCH OR DEVELOPMENT

This invention was made with government support under cooperative agreements awarded by the National Institutes of Health, Contract Nos. NIH RO1DK069764 and R01-DK74176. The U.S. government may have certain rights to the invention.

INCORPORATION BY REFERENCE OF SEQUENCE LISTING INFORMATION SUBMITTED ELECTRONICALLY

This application incorporates by reference the Sequence Listing filed electronically herewith as a text file entitled "SeqListing200512-70_ST25.txt" created on May 7, 2012 and consisting of 17,473 bytes.

BACKGROUND OF THE INVENTION

The stability of proteins used in medical treatment is an important concern in medicine. Protein degradation can be classified as physical or chemical degradation. Physical degradation is caused by a change in conformation that leads to aggregation of the protein and formation of protein fibrils. Chemical degradation of proteins entails a change in the pattern of covalent bonds between atoms, such as breakage or interchange of disulfide bridges, deamination or transamination of the protein. The present invention concerns the prevention of fibrillation and chemical degradation.

Administration of insulin has long been established as a treatment for diabetes mellitus. Insulin is a small globular protein that plays a central role in metabolism in vertebrates. Insulin contains two chains, an A chain, containing 21 residues and a B chain containing 30 residues. The hormone is stored in the pancreatic β-cell as a $Zn^{2+}$-stabilized hexamer, but functions as a $Zn^{2+}$-free monomer in the bloodstream. Insulin is the product of a single-chain precursor, proinsulin, in which a connecting region (35 residues) links the C-terminal residue of B chain (residue B30) to the N-terminal residue of the A chain (FIG. 1A). Although the structure of proinsulin has not been determined, a variety of evidence indicates that it consists of an insulin-like core and disordered connecting peptide (FIG. 1B). Formation of three specific disulfide bridges (A6-A11, A7-B7, and A20-B19; FIG. 1B) is thought to be coupled to oxidative folding of proinsulin in the rough endoplasmic reticulum (ER). Proinsulin assembles to form soluble $Zn^{2+}$-coordinated hexamers shortly after export from ER to the Golgi apparatus. Endoproteolytic digestion and conversion to insulin occurs in immature secretory granules followed by morphological condensation. Crystalline arrays of zinc insulin hexamers within mature storage granules have been visualized by electron microscopy (EM). Assembly and disassembly of native oligomers is thus intrinsic to the pathway of insulin biosynthesis, storage, secretion, and action (FIG. 2).

Insulin readily misfolds in vitro to form a prototypical amyloid. Unrelated to native assembly, fibrillation is believed to occur via an amyloidogenic partial fold (FIG. 1C). Factors that accelerate or hinder fibrillation have been extensively investigated in relation to pharmaceutical formulations. Zinc-free insulin is susceptible to fibrillation under a broad range of conditions and is promoted by factors that impair native dimerization and higher-order self-assembly. A storage form of insulin in the pancreatic β-cell and in the majority of pharmaceutical formulations is believed to be stabilized by axial zinc ions coordinated by the side chains of insulin amino acids, specifically the $His^{B10}$ residues. Formulation of insulin or insulin analogues as a zinc-stabilized hexamer retards but does not prevent fibrillation, especially above room temperature and on agitation.

Amino-acid substitutions in the A- and/or B chains of insulin have widely been investigated for possible favorable effects on the pharmacokinetics of insulin action following subcutaneous injection. Examples are known in the art of substitutions that accelerate or delay the time course of absorption. Such substitutions (such as $Asp^{B28}$ in the insulin analogue sold under the trademark NOVALOG® and [$Lys^{B28}$, $Pro^{B29}$] in the insulin analogue sold under the trademark HUMALOG®) can be and often are associated with more rapid fibrillation and poorer physical stability. Indeed, a series of ten analogues of human insulin for susceptibility to fibrillation, including $Asp^{B28}$-insulin and $Asp^{B10}$-insulin have been tested. All ten were found to be more susceptible to fibrillation at pH 7.4 and 37° C. than is human insulin. The ten substitutions were located at diverse sites in the insulin molecule and are likely to be associated with a wide variation of changes in classical thermodynamic stability. These results suggest that substitutions that protect an insulin analogue from fibrillation under pharmaceutical conditions are rare; no structural criteria or rules are apparent for their design. The present theory of protein fibrillation posits that the mechanism of fibrillation proceeds via a partially folded intermediate state, which in turn aggregates to form an amyloidogenic nucleus. In this theory, it is possible that amino-acid substitutions that stabilize the native state may or may not stabilize the partially folded intermediate state and may or may not increase (or decrease) the free-energy barrier between the native state and the intermediate state. Therefore, the current theory indicates that the tendency of a given amino-acid substitution in the insulin molecule to increase or decrease the risk of fibrillation is highly unpredictable.

Fibrillation, which is a serious concern in the manufacture, storage and use of insulin and insulin analogues for diabetes treatment, is enhanced with higher temperature, lower pH, agitation, or the presence of urea, guanidine, ethanol co-solvent, or hydrophobic surfaces. Current US drug regulations demand that insulin be discarded if fibrillation occurs at a level of one percent or more. Because fibrillation is enhanced at higher temperatures, diabetic individuals optimally must keep insulin refrigerated prior to use. Fibrillation of insulin or an insulin analogue can be a particular concern for diabetic patients utilizing an external insulin pump, in which small amounts of insulin or insulin analogue are injected into the patient's body at regular intervals. In such a usage, the insulin or insulin analogue is not kept refrigerated within the pump apparatus and fibrillation of insulin can result in blockage of the catheter used to inject insulin or insulin analogue into the body, potentially resulting in unpredictable blood glucose level fluctuations or even dangerous hyperglycemia. At least one recent report has indicated that lispro insulin (an analogue in which residues B28 and B29 are interchanged relative to their positions in wild-type human insulin; the product sold under the trademark HUMALOG®) may be particularly susceptible to fibrillation and resulting obstruction of insulin pump catheters.

Insulin fibrillation is an even greater concern in implantable insulin pumps, where the insulin would be contained within the implant for 1-3 months at high concentration and at physiological temperature (i.e. 37° C.), rather than at ambient temperature as with an external pump. Additionally, the agitation caused by normal movement would also tend to accelerate fibrillation of insulin. In spite of the increased potential for insulin fibrillation, implantable insulin pumps are still the subject of research efforts, due to the potential advantages of such systems. These advantages include intraperitoneal delivery of insulin to the portal circulatory system, which mimics normal physiological delivery of insulin more closely than subcutaneous injection, which provides insulin to the patient via the systemic circulatory system. Intraperitoneal delivery provides more rapid and consistent absorption of insulin compared to subcutaneous injection, which can provide variable absorption and degradation from one injection site to another. Administration of insulin via an implantable pump also potentially provides increased patient convenience. Whereas efforts to prevent fibrillation, such as by addition of a surfactant to the reservoir, have provided some improvement, these improvements have heretofore been considered insufficient to allow reliable usage of an implanted insulin pump in diabetic patients outside of strictly monitored clinical trials.

Resistance to fibrillation caused by heat or other causes would be particularly advantageous for insulin and insulin analogues in tropical and sub-tropical regions of the developing world. The major barrier to the storage and practical use of presently available pharmaceutical formulations of insulin and insulin analogues at temperatures above 30° C. is accelerated fibrillation of the protein. The major reason for limitations to the shelf life of presently available pharmaceutical formulations of insulin and insulin analogues at temperatures above 10° C. is due to fibrillation of the protein. As noted above, fibrillation is of special concern for fast-acting or "mealtime" insulin analogues (such as the products sold under the trademarks HUMALOG® and NOVALOG®), particularly when these formulations are diluted by the patient and stored at room temperature for more than 15 days.

Modifications of proteins such as insulin are known to increase resistance to fibrillation but impair biological activity. For example, "mini-proinsulin," is used to describe a variety of proinsulin analogues containing shortened linker regions such as a dipeptide linker between the A and B chains of insulin. Additional substitutions may also be present such as $Ala^{B30}$ found in porcine insulin instead of $Thr^{B30}$ as found in human insulin. This analogue is sometimes referred to as Porcine Insulin Precursor, or PIP. Mini-proinsulin analogues are frequently resistant to fibrillation but are impaired in their activity. In general, connecting peptides of length <4 residues block insulin fibrillation at the expense of biological activity; affinities for the insulin receptor are reported to be reduced by at least 10,000-fold. While such analogues are useful as intermediates in the manufacture of recombinant insulin, they are not useful per se in the treatment of diabetes mellitus. Therefore, a need exists for insulin analogues and other protein analogues that are resistant to fibrillation and that maintain at least a portion of their biological activity.

Development of fibrillation-resistant insulin analogues would not be expected to lead to proteins of indefinite shelf life due to eventual degradation of the protein by chemical modification. Whereas fibrillation represents a change in the structure and spatial relationships between insulin molecules by means of altered non-covalent interactions, chemical modification alters the pattern of covalent bonding between atoms in the insulin molecule. Examples of chemical degradation are breakage of disulfide bridges, formation of non-native disulfide bridges between insulin molecules to form covalent dimers and higher-order polymers, deamination of an asparagine side chain to form an aspartic-acid side chain, and rearrangement of aspartic acid to form iso-aspartic acid within the insulin molecule. Although the propensity of an insulin analogue to form fibrils is not correlated with its global thermodynamic stability, enhancing the thermodynamic stability of the insulin molecule has been established to protect the protein from chemical degradation. Therefore, among fibrillation-resistant analogues, a desirable property would also be enhanced thermodynamic stability to confer simultaneous protection from chemical degradation. The combination of resistance to fibrillation and resistance to chemical degradation would be expected to optimize the safe and effective use of an insulin analogue within the reservoir of an implantable insulin pump, the shelf life of an insulin analogue formulation at or above room temperature, and the routine use of an injectable insulin formulation by patients with diabetes mellitus in sub-tropical and tropical regions of the world.

Amino-acid substitutions in insulin have been investigated for effects on thermodynamic stability and biological activity. No consistent relationship has been observed between stability and activity. Whereas some substitutions that enhance thermodynamic stability also enhance binding to the insulin receptor, other substitutions that enhance stability impede such binding.

A traditional approach to protecting insulin or insulin analogues from physical and chemical degradation is based on self-assembly of the protein in its native state to form dimers or higher-order oligomers. Because the process of fibrillation proceeds via a conformationally altered insulin monomer, sequestration of the monomer within a native assembly reduces the concentration of the susceptible monomer. Such assembly also enhances thermodynamic stability, retarding chemical degradation. In addition, insulin assembly damps conformational fluctuations, reducing the rates of both physical and chemical degradation. Because of these advantages, a common method of formulation is to form zinc-stabilized insulin hexamers, the predominant form of the protein in the products sold under the trademarks HUMALIN™ (Eli Lilly and Co.), HUMALOG™ (Eli Lilly and Co.), NOVALIN™ (Novo-Nordisk), and NOVALOG™ (Novo-Nordisk). Use of insulin hexamers complicates the treatment of diabetes mellitus by delaying absorption of the protein after subcutaneous injection.

Glycemic control by insulin replacement therapy, whether administered by external pump, intraperitoneal pump, or manual subcutaneous injection, is enhanced by rapidly absorbed insulin analogues. Rapid absorption enables the time course of insulin action at target tissues to more nearly coincide with the time course of absorption of nutrients after a meal, hence more closely approximating the physiological control of blood glucose concentration and metabolism in a healthy (non-diabetic) person. Absorption of insulin is delayed by its self-assembly as in conventional formulations of human insulin and animal insulins as zinc-stabilized insulin hexamers. A partial solution to this problem has been provided by the meal-time insulin analogues in which the hexameric formulation is destabilized by amino-acid substitutions in the insulin molecule (see above). This approach is not optimal as the substitutions impair the physical stability and thermodynamic stability of the insulin analogue, leading to elevated rates of fibrillation and chemical degradation. Such decreased stability requires continued formulation as a zinc hexamer, leading in turn to a delay in absorption relative to injection of a monomeric insulin analogue. To date, no monomeric analogues have been developed that exhibit sufficient physical stability and thermodynamic stability to allow their formulation and therapeutic use. Therefore, a need exists for insulin analogues that combine the favorable properties of retaining at least partial biological activity, remaining monomeric in solution at millimolar protein concentrations in buffers compatible with pharmaceutical formulations, resisting fibrillation and other forms of non-native protein aggregation, and exhibiting enhanced thermodynamic stability to delay chemical degradation.

Insulin analogues with affinities too low or too high for the insulin receptor may have unfavorable biological properties in the treatment of diabetes mellitus. Because clearance of insulin from the bloodstream is mediated primarily by interactions with the insulin receptor on target tissues, receptor-binding activities less than 25% would be expected to exhibit prolonged lifetimes in the bloodstream. Such delayed clearance would be undesirable in a fast-acting insulin analogue administered in coordination with food intake for the tight control of glycemia. Such reduced affinities would also decrease the potency of the insulin analogue, requiring injection of either a larger volume of protein solution or use of a more highly concentrated protein solution.

Conversely, insulin analogues with affinities for the insulin receptor higher than that of wild-type insulin may be associated with altered signaling properties and altered cellular processing of the hormone-receptor complex. A prolonged residence time of the complex between the super-active insulin analogue and the insulin receptor on the surface of a target cell or on the surface of an intracellular vescicle may lead to elevated mitogenic signaling. Enhanced mitogenicity can occur if the amino-acid substitutions not only augment binding of the analogue to the insulin receptor, but also to the Type I IGF receptor. For these reasons, among fibrillation-resistant insulin analogues, it is desirable to have analogues whose affinities for the insulin receptor and IGF receptor are similar to those of wild-type human insulin.

A modification of insulin (substitution of $His^{B10}$ by Asp) has been described that enhances the thermodynamic stability of insulin and also augments its affinity for the insulin receptor by twofold. Because this substitution blocks the binding of zinc and prevents the assembly of insulin dimers into hexamers, it was investigated as a candidate fast-acting analog. Clinical development was stopped, however, when $Asp^{B10}$-insulin was found to exhibit increased mitogenicity, increased cross-binding to the insulin receptor, and elevated rates of mammary tumor formation on chronic administration to Sprague-Dawley rats. Because the otherwise favorable properties of $Asp^{B10}$-insulin and possibly other insulin analogues are confounded by these adverse properties, it would be desirable to have a design method to retain the favorable properties conferred by such substitutions while at the same time avoiding the adverse properties. A particular example would be re-design of the insulin molecule to retain the enhanced thermodynamic stability and receptor-binding properties associated with substitution of $His^{B10}$ by Asp without incurring increased cross-binding to the Type I IGF receptor or increased mitogenicity.

SUMMARY OF THE INVENTION

It is, therefore, an aspect of the present invention to provide insulin analogues that are more resistant to fibrillation than their wild-type counterparts, while maintaining at least a portion of the wild type biological activity.

It is another aspect of the present invention to provide insulin analogues that are more resistant to fibrillation than their counterpart insulins but maintain at least a majority of their biological activity. In one example, a fibrillation-resistant insulin analogue displays less than one percent fibrillation with incubation and agitation at 37° C. for at least 21 days and maintains at least a majority of the affinity for insulin receptor of wild type insulin. In another example, a fibrillation-resistant insulin analogue displays less than one percent fibrillation with incubation and agitation at 37° C. for at least 30 days and maintains at least a majority of the affinity for insulin receptor of wild type insulin. In still another example, a fibrillation-resistant insulin analogue displays less than one percent fibrillation with incubation and agitation at 37° C. for at least 60 days. In yet another example, a fibrillation-resistant insulin analogue displays less than one percent fibrillation with incubation and agitation at 37° C. for at least 60 days and maintains at least a majority of the insulin receptor affinity of wild type insulin. In still another example, a fibrillation-resistant insulin analogue displays less than one percent fibrillation with incubation and agitation at 37° C. for at least 90 days. In yet another example, a fibrillation-resistant insulin analogue displays less than one percent fibrillation with incubation and agitation at 37° C. for at least 180 days and maintains at least a majority of the affinity for insulin receptor of wild type insulin. This analogue also exhibits enhanced thermodynamic stability and is refractory to chemical degradation (other than deamination of asparagine) for at least 180 days.

It is yet another aspect of the present invention to combine amino-acid substitutions in the A- and B-chains of insulin with a linker peptide sequence such that the isoelectric point of the monomeric protein is similar to or less than that of wild-type human insulin, thereby preserving the solubility of the protein at neutral pH conditions.

It is yet another aspect of the present invention to provide a nucleic-acid sequence that encodes for at least a portion of a single-chain insulin analogue that displays increased resistance to fibrillation compared to a corresponding two-chain insulin. In particular, it is an aspect of the present invention to provide an insulin analogue comprising a single chain polypeptide of formula I,

B-C-A     (I)

where B comprises a polypeptide having the sequence:

(SEQ ID NO: 33)
FVNQHLCGSX$_2$LVEALYLVCGERGFFYTX$_3$ X$_4$T where $X_2$ is D or H, $X_3$ is P, D or K, and $X_4$ is K or P, and where C is a polypeptide selected from the group consisting of a polypeptide having the sequence GGGPRR (SEQ ID NO: 19) and a polypeptide having the sequence GGPRR (SEQ ID NO: 20), and where A comprises a polypeptide having the sequence:

(SEQ ID NO: 32)
GIVEQCCX$_1$SICSLYQLENYCN, where $X_1$ is T or H.

It is still another aspect of the present invention to provide a method treating a mammal, such as a human, comprising administering a physiologically effective amount of a single chain insulin analogue to the mammal. The single chain insulin analogue comprises an insulin A chain polypeptide connected to an insulin B chain polypepetide by a connecting polypeptide comprising 4-10 amino acids. In one particular example, the connecting polypeptide is a polypeptide selected from the group consisting of a polypeptide having the sequence GGGPRR (SEQ ID NO: 19) and a polypeptide having the sequence GGPRR (SEQ ID NO: 20). Additionally or in the alternative, the insulin B chain polypeptide may contain an asparagine substitution at position B10. The binding affinity of the single chain insulin for insulin-like growth factor receptor is essentially equal to or less than the binding affinity of human insulin for insulin-like growth factor receptor. Further additionally or in the alternative, the insulin A chain polypeptide may comprise a histidine substitution at position A10. IN one particular example, the single chain insulin analogue is a polypeptide having the sequence FVN-QHLCGSNLVEALYLVCGERGFFYT-NPTGGGPRRGIVEQCCHSICSLYQLENYCN (SEQ ID NO: 26). In another example, the insulin is administered by an external or implantable insulin pump.

It is still another aspect of the present invention to provide a molecular design to prevent a significant increase in cross-binding by an insulin analogue to the Type I IGF receptor and to prevent a significant increase in mitogenicity, including in stimulation of the growth of human cancer cells in cell culture. A linker between the A- and B-chains of an insulin analogue can be interposed to reduce such cross-binding and mitogenicity otherwise conferred on two-chain insulin analogues by certain amino-acid substitutions in the A- or B-chains.

In general, the present invention provides a vertebrate insulin analogue or a physiologically acceptable salt thereof, comprising a single-chain insulin analogue containing an insulin A chain and an insulin B chain connected by a truncated linker. In one example, the linker may be less than 15 amino acids long. In other examples, the linker may be 4, 5, 6, 7, 8, 9, or 10 amino acids long. A single-chain insulin analogue of the present invention may also contain other modifications, such as substitutions of a histidine at residues A4, A8 and B1 as described more fully in co-pending U.S. application Ser. No. 12/160,187, the disclosure of which is incorporated by reference herein. In one example, the vertebrate insulin analogue is a mammalian insulin analogue, such as a human, porcine, bovine, feline, canine or equine insulin analogue.

The present invention likewise provides a pharmaceutical composition comprising such insulin analogues and which may optionally include zinc. Zinc ions may be included in such a composition at a level of a molar ratio of between 2.2 and 3.0 per hexamer of the insulin analogue. In such a formulation, the concentration of the insulin analogue would typically be between about 0.1 and about 3 mM; concentrations up to 3 mM may be used in the reservoir of an insulin pump. In another example, a pharmaceutical composition including a single-chain insulin analogue displays less than 1 percent fibrillation at 37° C. at a zinc molar ratio of less than 2, 1.5, 1 per hexamer or even in the absence of zinc other than that amount present as an impurity.

The fast-acting analogue Glulisine-insulin (sold under the trademark APIDRA®; Sanofi-Aventis Pharmaceuticals) is an example of a zinc-free formulation; the analogue presumably exists as an equilibrium containing dimers, trimers, tetramers and hexamers whose rapid dissociation (relative to zinc-stabilized hexamers) facilitates absorption after subcutaneous injection. A long-sought but unmet goal is the development of monomeric and zinc-free insulin formulations. Subcutaneous injection of a monomeric formulation would be the ultimate in rapidity of absorption, a favorable feature for use in exter- nal or implantable pumps. The barrier to use of monomeric formulations in the past has been their enhanced rate of fibrillation. This barrier has seemed to be intrinsic to the structure of the insulin molecule since the monomer is the species most susceptible to fibrillation. The present invention provides a combination of single-chain tethers between A and B chains and amino-acid substitutions in the A and B chains that may be used to obtain a monomeric formulation that is active and highly resistant to fibrillation, even at 37° C.

Excipients may include glycerol, Glycine, other buffers and salts, and anti-microbial preservatives such as phenol and meta-cresol; the latter preservatives are known to enhance the stability of the insulin hexamer. Such a pharmaceutical composition may be used to treat a patient having diabetes mellitus or other medical condition by administering a physiologically effective amount of the composition to the patient.

The present invention also provides a nucleic acid comprising a sequence that encodes a polypeptide encoding a single-chain insulin analogue containing a sequence encoding an A chain, a B chain and a linker between the A and B chains containing 4-15 codons. The nucleic acid may also encode other modifications of wild-type insulin such as histidine residue substitutions at residues A4 and A8, a histidine residue substitution at residue B1, and combinations thereof. Residues other than histidines may be substituted at position A8 or B10 to enhance stability and activity. The nucleic acid sequence may encode a modified A- or B chain sequence containing an unrelated substitution or extension elsewhere in the polypeptide or modified proinsulin analogues. The nucleic acid may also be a portion of an expression vector, and that vector may be inserted into a host cell such as a prokaryotic host cell like an *E. coli* cell line, or a eukaryotic cell line such as as *S. cereviciae* or *Pischia pastoris* strain or cell line.

Chemical degradation of insulin, such as deamination, isopeptide bond formation, and disulfide interchange leading to formation of covalent polymers, is known to be reduced by formulations or modifications that enhance the thermodynamic stability of the native molecular structure of the insulin or insulin analogue. Such degradation may also be reduced by formulations or modifications that damp the conformational flexibility of the insulin molecule. Introduction of a truncated linker region in a single-chain insulin analogue may confer an increase in thermodynamic stability and/or reduce conformational flexibility and so delay chemical degradation of the protein. Further increases in thermodynamic stability in the context of a single-chain analogue may be obtained by substitutions at residues A8, B10 or both.

BRIEF DESCRIPTION OF THE SEVERAL
VIEWS OF THE DRAWINGS

FIG. 1A is a schematic representation of the sequence of human proinsulin (SEQ ID NO: 1) including the A and B chains and the connecting region shown with flanking dibasic cleavage sites (filled circles) and C-peptide (open circles). The line labeled "foreshortened connecting peptide" represents the connecting region in mini-proinsulin, which is a proinsulin analogue containing a dipeptide (Ala-Lys) linker between the A chain and B chain portions of insulin.

FIG. 1B provides a structural model of proinsulin, consisting of an insulin-like moiety and disordered connecting peptide (dashed line). The asterisk indicates foreshortened AK linker in mini-proinsulin.

FIG. 1C provides a representation of a proposed pathway of insulin fibrillation via partial unfolding of monomer. The native state is protected by classic self-assembly (far left). Disassembly leads to equilibrium between native- and partially folded monomers (open triangle and trapezoid, respectively). This partial fold may unfold completely as an off-pathway event (open circle) or aggregate to form a nucleus en route to a protofilament (far right).

FIG. 2 is a representation of the pathway of insulin biosynthesis, storage, and secretion. A, nascent proinsulin folds as a monomer in ER wherein zinc-ion concentration is low; in Golgi apparatus zinc-stabilized proinsulin hexamer assembles, which is processed by cleavage of connecting peptide to yield mature insulin. Zinc-insulin crystals are observed in secretory granules. B, on metabolic stimulus, zinc-insulin crystals are released into portal circulation and disassociate in steps to liberate the functional monomer.

FIG. 3A is a series of HPLC chromatograms of aliquots of a single-chain insulin analogue incubated at 37° C. with gentle agitation from 0-109 days. FIG. 3B is a series of Matrix Assisted Laser Desorption/Ionization-Time of Flight (MALDI-TOF) mass spectra of the same samples as in FIG. 3A. *R and *B represent major peak (native analog) and minor degradation products in FIGS. 3A and 3B.

FIG. 4 is a graph of the results of a receptor-binding assay in which binding of the 57 mer single-chain insulin analogue (dashed line; triangles) was evaluated relative to native human insulin (solid line; squares) using human placental membranes containing a mixture of isoforms A and B of the insulin receptor. This assay measures the displacement of receptor-bound $^{125}$I-labeled insulin by either unlabeled analogue or unlabelled insulin.

FIG. 5 is a ribbon representation of the NMR structure of a synthetic 57 mer single-chain insulin analogue (panel D) in relation to the NMR structure of a synthetic 51 mer two-chain insulin analogue containing the same four substitutions in the A- and B-chains (panel C), a crystallographic T-state protomer extracted from the classical $T_6$ insulin hexamer (A; Protein Database accession code 4INS) and NMR structure of an engineered insulin monomer (B; "DKP-insulin," Protein Database accession code 2JMN). In each case the A- and B-chains (or domains) are shown in dark and light gray, respectively.

DETAILED DESCRIPTION OF THE INVENTION

Figure 1A:
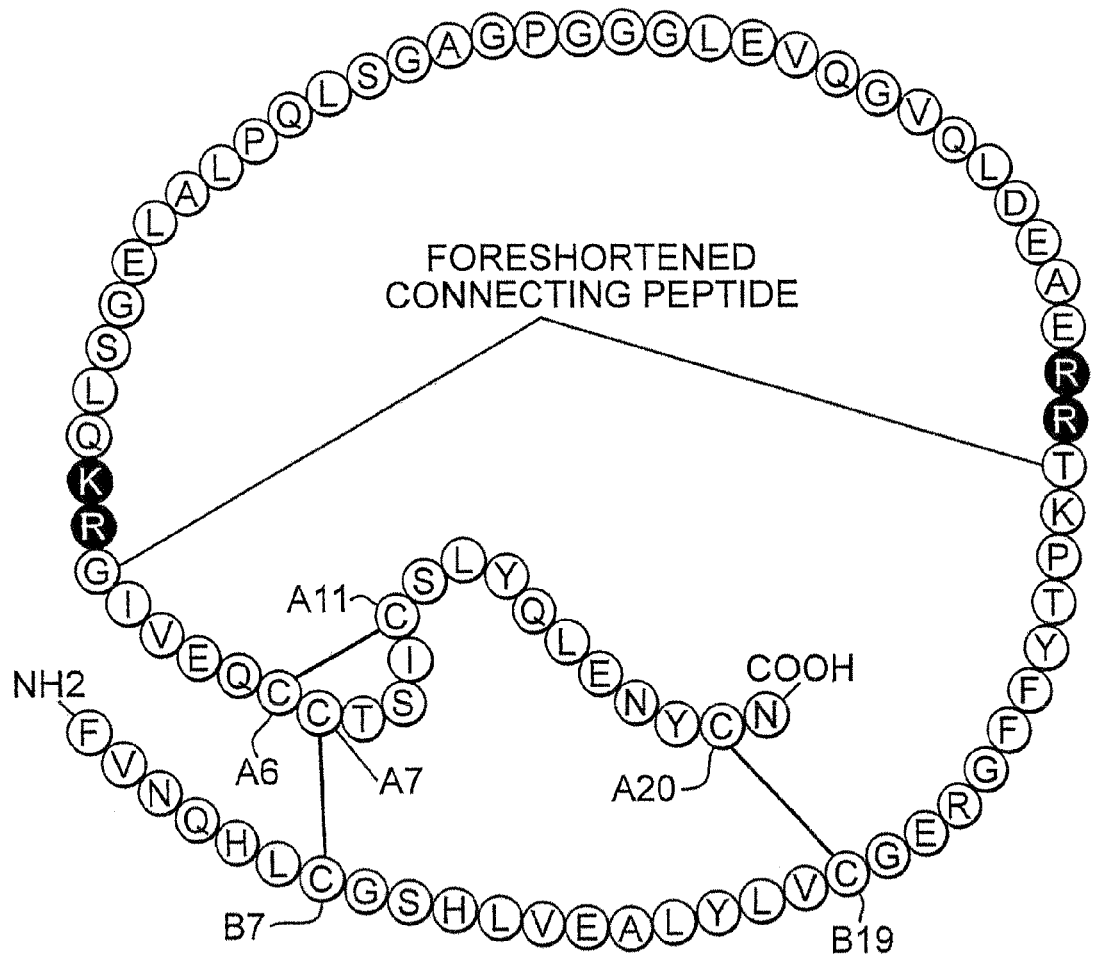
Figure 1B:
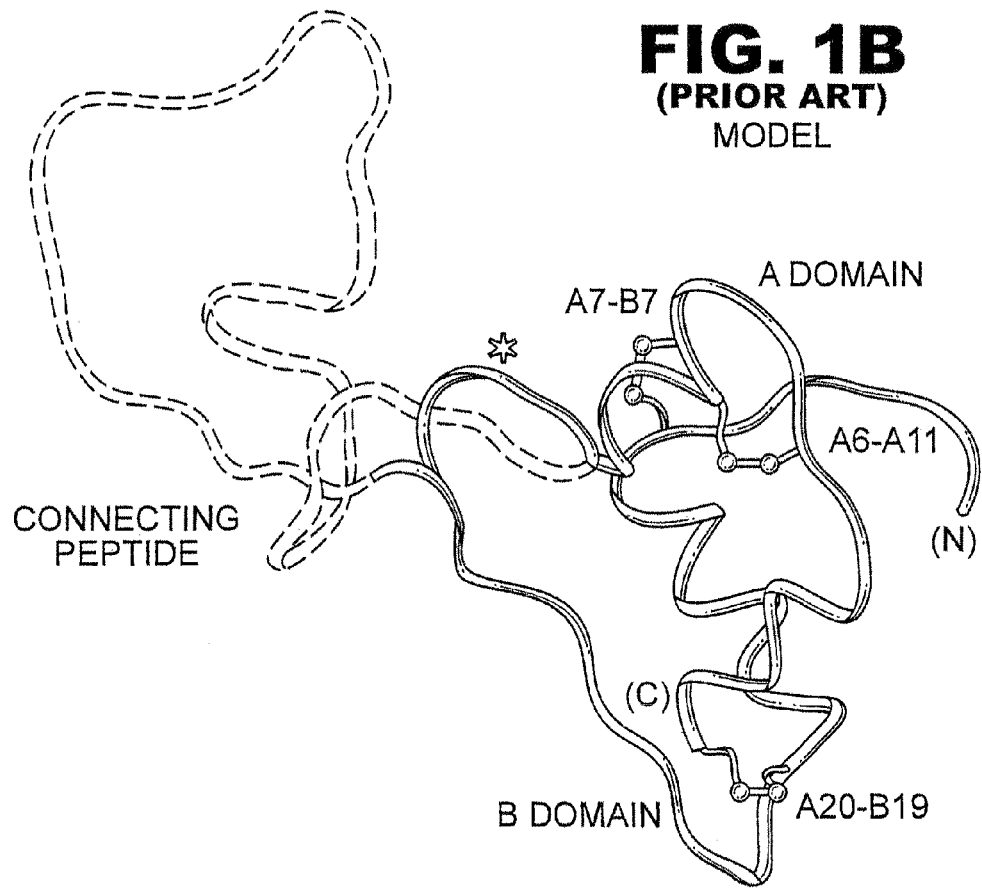
Figure 1C:
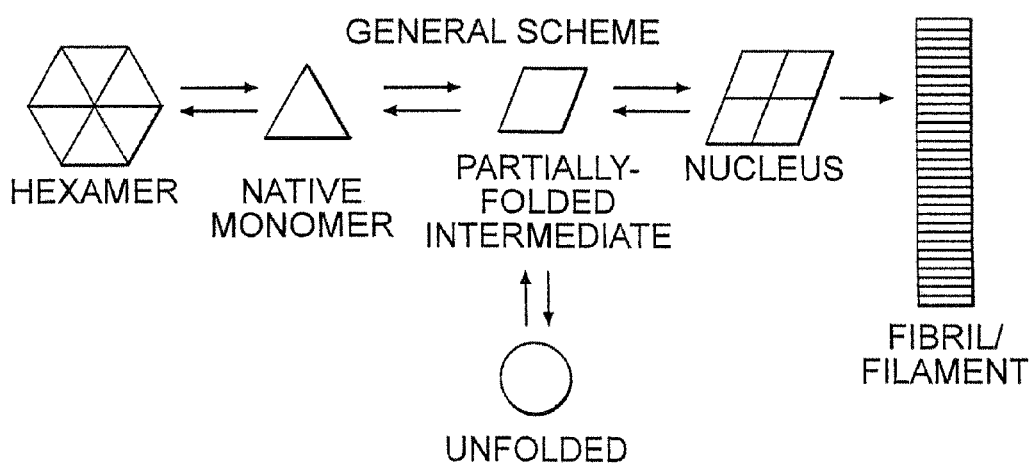
Figure 2:
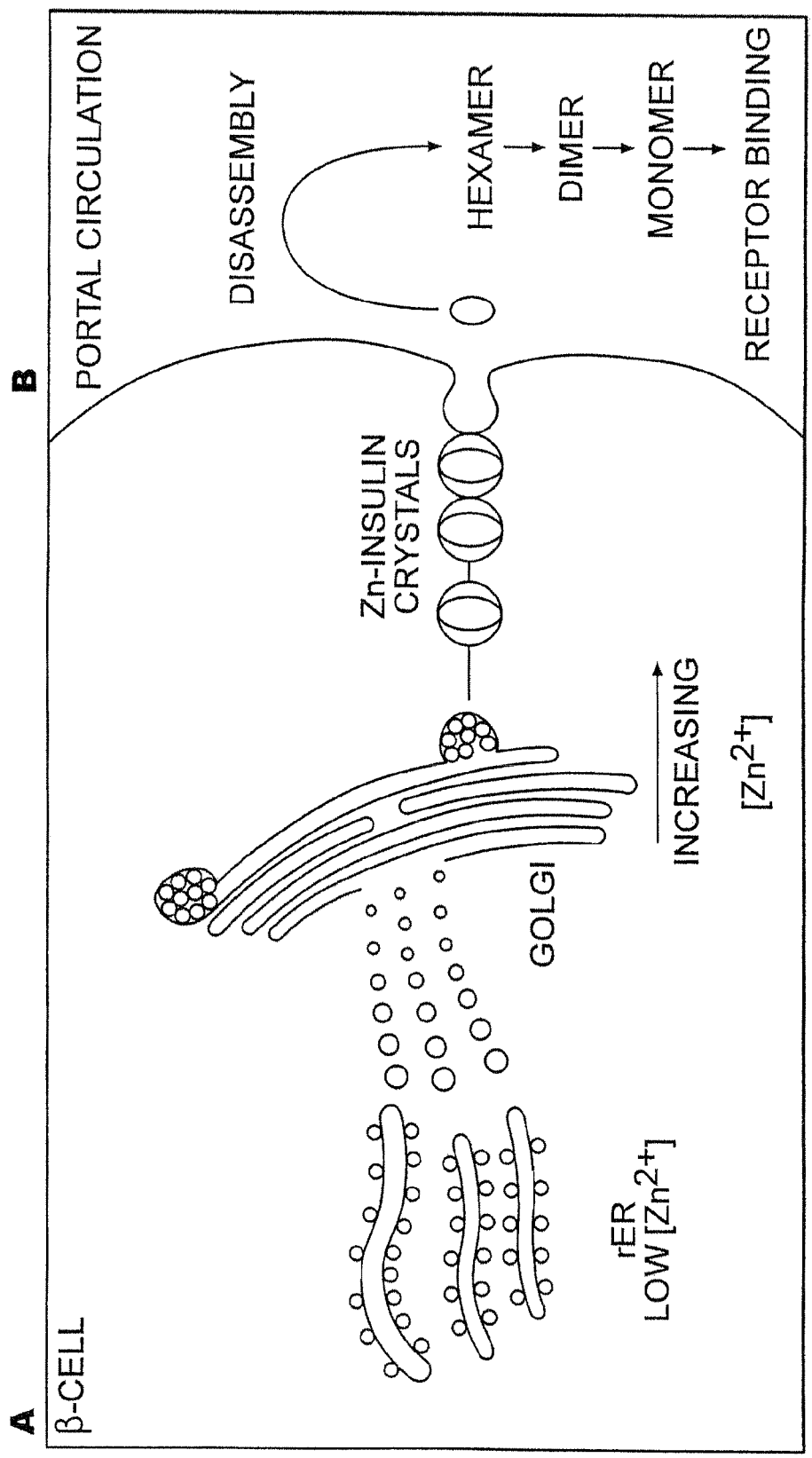

The present invention is directed toward recombinant single-chain insulin analogues that provide increased resistance to fibrillation and their use in treatment of diabetes, particularly their use in insulin delivery via implantable or external pumps. To that end, the present invention provides insulin analogues that contain an insulin A-chain polypeptide and an insulin B-chain polypeptide connected by a truncated linker polypeptide. In one example, the linker polypeptide may be less than 15 amino acids long. In other examples, the linker polypeptide may be 4, 5, 6, 7, 8, 9, or 10 amino acids long.

The single-chain insulin analogue of the present invention may also contain other modifications. As used in this specification and the claims, various substitution analogues of insulin may be noted by the convention that indicates the amino acid being substituted, followed by the position of the amino acid, optionally in superscript. The position of the amino acid in question includes the A or B chain of insulin where the substitution is located. For example, the single-chain insulin analogue of the present invention may also contain a substitution of aspartic acid (Asp or D) or lysine (Lys or K) for proline (Pro or P) at amino acid 28 of the B chain (B28), or a substitution of Pro for Lys at amino acid 29 of the B chain (B29) or a combination thereof. These substitutions may also be denoted as Asp$^{B28}$, Lys$^{B28}$, and Pro$^{B29}$, respectively. Unless noted otherwise or wherever obvious from the context, the amino acids noted herein should be considered to be L-amino acids.

Another aspect of this invention is the use of a linker between modified A- and B-chains of insulin simultaneously to enable (a) optimization of resistance to fibrillation, (b) hindrance of native self-assembly to permit formulation of a monomeric analogue at millimolar protein concentrations, (c) enhanced thermodynamic stability and hence chemical stability, (d) native or near-native biological activity, (d) avoidance of significantly increased cross-binding to the IGF Type I receptor, and (e) avoidance of significantly increased mitogenicity.

The Asp$^{B28}$ substitution is present in the insulin analogue known as Aspart insulin and sold under the trademark NOVA-LOG® whereas the Lys$^{B28}$ and Pro$^{B29}$ substitutions are present in the insulin analogue known as Lispro insulin and sold under the trademark HUMALOG®. These analogues are described in U.S. Pat. Nos. 5,149,777 and 5,474,978, the disclosures of which are hereby incorporated by reference herein. Both of these analogues are known as fast-acting insulins, but are also known to have increased propensity to aggregate and form fibrils. Therefore, it is envisioned that the fibril-resistant single-chain insulin analogues of the present invention will increase the usefulness of insulin analogues also carrying substitutions, such as the Asp$^{B28}$ or Lys$^{B28}$, Pro$^{B29}$ substitutions, for example.

It is also possible for additions to be made to an insulin polypeptide. For example, the insulin analogue sold under the trademark LANTUS® contains two additional Arg residues added to the carboxy-terminal end of the B-chain in addition to an Asp$^{A21}$ substitution.

It is also envisioned that the receptor-binding activity of a single-chain insulin analogue, ordinarily reduced by the connecting domain even when of length 5-15 residues, can be in part or wholly restored by appropriate amino-acid substitutions in the A- and/or B domain. Examples of such substitutions are replacement of Thr by His at position A8 and replacement of His by Asp at position B10.

It is further envisioned that truncated connecting domains in single-chain insulin analogues can be designed to reduce cross-binding of the analogue to the IGF Type I receptor and hence the mitogenicity and potential carcinogenicity of the analogue. An appropriate foreshortened connecting peptide may thus permit incorporation of amino-acid substitutions within the A- or B domain of the single-chain insulin analogue that would otherwise (in the context of a two-chain analogue) lead to a significant increase to cross-binding to the IGF Type I receptor. An example of such a substitution is replacement of His by Asp at position B10. Amino-acid substitutions that enhance the affinity of a two-chain insulin analogue can also be associated with a prolonged residence time within the hormone-receptor complex. An appropriately designed foreshortened connecting peptide can tune the affinity of such an analogue to more nearly resemble that of native human insulin and thereby avoid any changes in cellular signalling associated with a prolonged residence time when the analogue is bound to the insulin receptor.

The single-chain insulin analogues of the present invention may also contain substitutions that were previously considered unsuitable for use in human subjects. For example, the substitution of Asp for histidine (His or H) at amino acid 10 of the B chain ($Asp^{B10}$), mentioned above, is known to preclude zinc binding and hexamer formation, accelerate absorption after subcutaneous injection, stabilize insulin monomers and enhance activity over that of non-analogue insulin. This insulin analogue has been described as "superactive" in U.S. Pat. Nos. 4,992,417 and 4,992,418, the disclosures of which are incorporated herein by reference. As mentioned therein, the superactivity of the $Asp^{B10}$ analogue is thought to be due to greater affinity of the analogue of the insulin receptor than natural insulin. However, this insulin analogue is not suitable for clinical use because the analogue also has enhanced affinity for the insulin-like growth factor type I receptor (IGFR) resulting increased mitogenicity. It is envisioned that the truncated linker in the single-chain insulin analogues of the present invention may be designed to interfere with binding of the insulin analogue to IGFR, thereby providing a fast acting, $Asp^{B10}$ insulin analogue that resists fibrillation but also poses no risk of inducing cancer by activation of IGFR beyond that of natural insulin. To that end, it may be advantageous to utilize a linker that does not contain the sequence Arg-Arg-$Xaa_{2-8}$ or Tyrosine with tandem arginines as present in the Insulin-like Growth Factor 1 (IFG-1) C-domain because these sequences have been identified as being important for binding of IFG-1 to IGFR.

Still other substitutions are also compatible with the single-chain insulin analogues of the present invention. As mentioned above, His substitutions at A4, A8 and B1 are described in U.S. application Ser. No. 12/160,187, the disclosure of which is incorporated by reference herein. While not wishing to be bound by theory, it is believed that when the $His^{B1}$ substitution is present, the side chain of the B1 His residue, in combination with the B5 histidine side chain, provides a potential B1-B5 bi-Histidine Zn-binding site, which confers Zn-dependent protection from fibrillation. Similarly, while not wishing to be bound by theory, it is believed that the [$His^{A4}$, $His^{A8}$] substitutions also provide a potential bi-histidine Zn-binding site, which also confers protection from fibrillation. It is further envisioned that zinc stabilization of insulin will not affect activity in vivo because such zinc-protein structures are predicted to dissociate at protein and zinc concentrations less than about 1 μM. The protective effect of zinc binding may be mediated either though binding to the native molecular structure or to a distorted molecular structure as is thought to occur as an intermediate in the process of fibrillation.

It is also envisioned that the intrinsic resistance of these single-chain insulin analogues to fibrillation makes it unnecessary to formulate such analogues as zinc-stabilized hexamers or other higher-order oligomers. Because disassembly of the zinc-stabilized hexamer ordinarily delays absorption of insulin or insulin analogues in current formulations, it is envisioned that a fibrillation-resistant formulation of a single-chain insulin analogue as a zinc-free insulin monomer or dimer would confer more rapid adsorption into the blood stream following subcutaneous injection or more rapid absorption into the portal circulation following intraperitoneal delivery by an implantable insulin pump.

It is further envisioned that the single-chain insulin analogues of the present invention may also utilize any of a number of changes present in existing insulin analogues, modified insulins, or within various pharmaceutical formulations, such as regular insulin, NPH insulin, lente insulin or ultralente insulin, in addition to human insulin. The single-chain insulin analogues of the present invention may also contain substitutions present in analogues of human insulin that, while not clinically used, are still useful experimentally, such as DKP-insulin, which contains the substitutions $Asp^{B10}$, $Lys^{B28}$ and $Pro^{B29}$ or the $Asp^{B9}$ substitution. The present invention is not, however, limited to human insulin and its analogues. It is also envisioned that these substitutions may also be made in animal insulins such as porcine, bovine, equine, and canine insulins, by way of non-limiting examples. Furthermore, in view of the similarity between human and animal insulins, and use in the past of animal insulins in human diabetic patients, it is also envisioned that other minor modifications in the sequence of insulin may be introduced, especially those substitutions considered "conservative" substitutions. For example, additional substitutions of amino acids may be made within groups of amino acids with similar side chains, without departing from the present invention. These include the neutral hydrophobic amino acids: alanine (Ala or A), valine (Val or V), leucine (Leu or L), isoleucine (Ile or I), proline (Pro or P), tryptophan (Trp or W), phenylalanine (Phe or F) and methionine (Met or M). Likewise, the neutral polar amino acids may be substituted for each other within their group of glycine (Gly or G), serine (Ser or S), threonine (Thr or T), tyrosine (Tyr or Y), cysteine (Cys or C), glutamine (Glu or Q), and asparagine (Asn or N). Basic amino acids are considered to include lysine (Lys or K), arginine (Arg or R) and histidine (His or H). Acidic amino acids are aspartic acid (Asp or D) and glutamic acid (Glu or E). In one example, the insulin analogue of the present invention contains three or fewer conservative substitutions other than the modified linker of the present invention. In another example, the insulin analogue of the present invention contains one or fewer conservative substitutions other than the modified linker of the present invention.

The amino acid sequence of human proinsulin is provided, for comparative purposes, as SEQ ID NO: 1. The amino acid sequence of the A chain of human insulin is provided as SEQ ID NO: 2. The amino acid sequence of the B chain of human insulin is provided, for comparative purposes, as SEQ ID NO: 3. The amino acid sequence of a single-chain human insulin of the present invention is provided as SEQ ID NO: 4, where Xaa represents any amino acid. In various examples, the linker represented by Xaa may be 4, 5, 6, 7, 8, 9, or 10 amino acids in length. In one example, the linker comprises the naturally occurring amino acids that immediately flank the A and B chains. SEQ ID NOS: 5-14 provide sequences where the linker comprises amino acids in their naturally occurring locations in proinsulin. Stated another way, the natural linker of proinsulin is truncated in varying amounts, leaving amino acids naturally found immediately adjacent to the A and B chains in proinsulin. In SEQ ID NO: 5, the Arg residues immediately flanking the A and B chains are present. In SEQ ID NO: 6, the two Arg residues normally found adjacent the B chain and the Arg and Lys residues normally found adjacent the A chain are present. In SEQ ID NOS: 7 and 8, the Arg-Arg-Glu sequence normally found adjacent the B chain and the Gln-Lys-Arg sequence normally found adjacent the A chain are present. In SEQ ID NO: 7 an additional 1-4 amino acids may optionally be present. SEQ ID NOS: 9-14 provide linkers of varying lengths, consisting of various sequences found naturally in the sequence of proinsulin.

Other truncated linkers, with sequences not found naturally in insulin, may also be utilized. For example, SEQ ID NO: 19 provides a linker having the sequence Gly-Gly-Gly-Pro-Arg-Arg, SEQ ID NO: 20 provides a linker having the sequence Gly-Gly-Pro-Arg-Arg, SEQ ID NO: 21 provides a linker having the sequence Gly-Ser-Glu-Gln-Arg-Arg, SEQ ID NO: 22 provides a linker having the sequence Arg-Arg-Glu-Gln-Lys-Arg, SEQ ID NO: 23 provides a linker having the sequence Arg-Arg-Glu-Ala-Leu-Gln-Lys-Arg, SEQ ID NO: 24 provides a linker having the sequence Gly-Ala-Gly-Pro-Arg-Arg, SEQ ID NO: 25 provides a linker having the sequence Gly-Pro-Arg-Arg and SEQ ID NO: 30 provides a linker having the sequence Gly-Gly-Gly-Pro-Gly-Lys-Arg. It is envisioned that any of these truncated linkers may be used in the single-chain insulin analogues of the present invention, either alone or in combination with other substitutions or other changes in the insulin polypeptide sequence as noted herein.

Various substitutions, including substitutions of prior known insulin analogues, may also be present in the single-chain insulin analogue of the present invention. For example, an amino acid sequence of a single-chain insulin analogue also carrying the $Lys^{B28}Pro^{B29}$ substitutions of lispro insulin is provided as SEQ ID NO:15. Likewise, an amino acid sequence of a single-chain insulin analogue also carrying the $Asp^{B28}$ substitution of aspart insulin is provided as SEQ ID NO:16. Additionally, exemplary amino acid sequences of single-chain insulin analogues also carrying the $Asp^{B10}$ substitution are provided as SEQ ID NOS: 17 and 18.

The increased activity of the $Asp^{B10}$ substitution, together with the altered three-dimensional structure of the single-chain analogue of the present invention provides an insulin analogue that has increased activity compared to natural insulin but does not have an affinity for Insulin-like Growth Factor Receptor that is more than twofold higher than that of normal insulin. Insulin or insulin analogue activity may be determined by receptor binding assays as described in more detail herein below. Relative activity may be defined in terms of $ED_{50}$ values, the concentration of unlabelled insulin or insulin analogue required to displace 50 percent of specifically bound labeled human insulin such as a radioactively-labeled human insulin (such as $^{125}$I-labeled insulin) or radioactively-labeled high-affinity insulin analog. Alternatively, activity may be expressed simply as a percentage of normal insulin. Affinity for the insulin-like growth factor receptor may also be determined in the same way with displacement from IGFR being measured. In particular, it is desirable for single-chain insulin analogue to have an activity that is greater than 100 percent of insulin, such as 110, 120, 130, 140, 150, or 200 percent of normal insulin or more, while having an affinity for IGFR that is less than or equal to 100 percent of normal insulin, such as 90, 80, 70, 60 or 50 percent of normal insulin or less. It is desirable to determine insulin activity in vitro as described herein, rather than in vivo. It has been noted that in vivo, clearance of insulin from the bloodstream is dependent on receptor binding. In this way, insulin analogues may exhibit high activity, even approaching approximately 100 percent activity in vivo, even though they are less active at the cellular level, due to slower clearance from the bloodstream. However, an insulin analogue can still be useful in the treatment of diabetes even if the in vitro receptor-binding activity is as low as 20% due to this slower clearance. In such examples, the single-chain insulin analogue may have the sequence of SEQ ID NOS: 4, 15, 16 or 17, where the first two amino acids of $Xaa_{4-10}$ are amino acids other than Arg.

A single-chain analogue of insulin having the polypeptide sequence of SEQ ID NO: 26 was made by total chemical synthesis using thiol-ester-mediated native fragment ligation of three polypeptide segments. The segments comprised residues 1-6 (segment I), 7-42 (segment II), and 43-57 (segment III). Each segment was synthesized by the solid-phase method. Segments I and segment II were prepared by N-α-tert-butyloxycarbonyl (Boc)-chemistry on $OCH_2$-Pam resin (Applied Biosystems); segment III was prepared by N-α-(9-fluoronylmethoxycarbonyl (Fmoc)-chemistry on Polyethylene Glycol-Polystyrene (PEG-PS) resin with standard side-chain protecting groups. Segment I was synthesized as a thioester (beta-mercaptoleucine, βMp-Leu). The synthesis was started from Boc-Leu-$OCH_2$-Pam resin, and the peptide chain was extended stepwise to the N-terminal residue. Segment II was also synthesized as a thioester with peptide, Arg-Arg-Gly, attached at the C-terminal of βMp-residue to enhance solubility of the segment. The N-terminal amino acid, Cysteine, of segment II was protected as thiazolidine (Thz) and converted to Cysteine by $MeONH_2$.HCl after the ligation. Following native ligation, the full-length polypeptide chain was allowed to fold in a mixture of 100 mM reduced glutathione (GSH) and 10 mM oxidized glutathione (GSSG) at pH 8.6 and subjected to HPLC purification using C4 column (1.0×25 cm) at the gradient elution from 15% to 35% (A/B) over 40 min at the flow rate of 4 ml/min. The pure fractions corresponding to SCI (1) were pooled and freeze-dried. The predicted molecular mass was verified by mass spectrometry.

Additionally, a single chain insulin having the polypeptide sequence of SEQ ID NO: 31 was also synthesized as provided above. For comparative purposes, a two-chain insulin analogue was synthesized containing the same four substitutions as in the A- and B-domains of the above single-chain analogue ($His^{A8}$, $Asp^{B10}$, $Asp^{B28}$, and $Pro^{B29}$). This two-chain analogue thus contains a modified A-chain of 21 residues (SEQ ID NO: 29) and a modified B-chain of 30 residues (SEQ ID NO: 28), the same chain lengths as are present in wild-type human insulin. Comparison of the properties of the two-chain analogue with human insulin indicates the intrinsic effects of the four substitutions. Comparison of the properties of the single-chain analogue and two-chain analogue indicates how these altered properties are modulated by the interposition of a peptide linker between chains. Together, the amino-acid substitutions in the A- and B-chains and the amino-acid-sequence of the linker confer electrostatic balance, enabling the single-chain analog to retain an isoelectric point similar to that of wild-type human insulin. Thus, the two additional positive charges introduced by the two Arg residues in the linker and the partial positive charge introduced by substitution of Thr$^{A8}$ by His are offset by the introduction of negative charges by Asp$^{B10}$ and Asp$^{B28}$ and by the removal of the positive charge of Lys$^{B29}$ and the partial positive charge of His$^{B10}$. The isoelectric point is thus predicted to be slightly lower (i.e., more acidic) than that of wild-type human insulin, which would be expected to enhance solubility at neutral pH. The amino-acid sequence of the single-chain analogue also lacks positive charges in the segment B28-B32, which would otherwise favor binding to the Type I IGF receptor.

The 57-mer single-chain analogue having the polypeptide sequence of SEQ ID NO: 26, was synthesized and tested for activity and resistance to fibrillation as provided herein in comparison to human insulin, Asp$^{B10}$-human insulin, His$^{A8}$-human insulin, and the fast-acting analogue in HUMALOG (i.e. in which Pro at position B28 is replaced by Lys, and Lys at position B29 is replaced by Pro). Fibrillation was assayed under zinc-free conditions to highlight the novel feasibility of formulating the present 57 mer single-chain analogue as a fibrillation-resistant monomer; i.e. protection by assembly into a zinc-stabilized hexamer is not necessary to achieve long-term stability at elevated temperature. Further, because even in hexameric solutions the monomer is the susceptible species in the mechanism of fibrillation, linker-specific protection from fibrillation in a monomeric analogue predicts comparable or greater protection in a hexameric formulation. As a control, a two-chain insulin analogue was prepared.

Figure 3A:
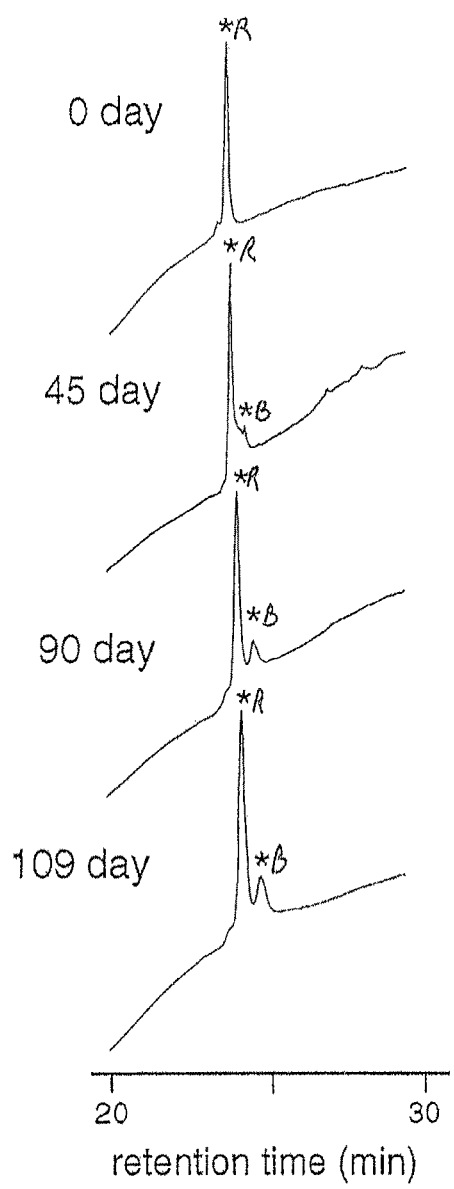
Figure 3B:
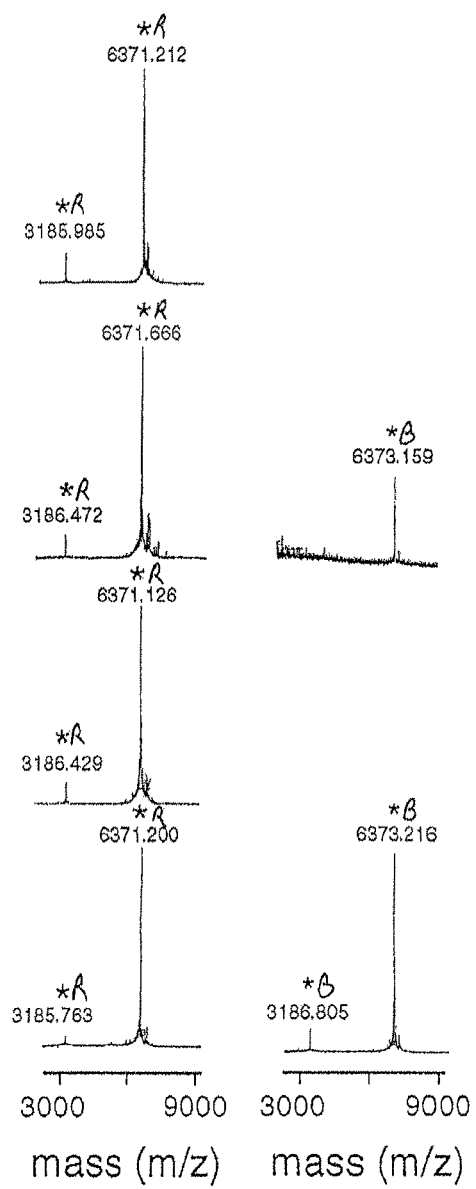

The physical and chemical stabilities of the single-chain analogue were evaluated in triplicate during incubation in 60 μM phosphate-buffered saline (PBS) at pH 7.4 at 37° C. under gentle agitation. The samples were observed for 109 days. The three samples showed physical stability, remaining clear with no sign of precipitation or frosting of the glass vial. Inspection of aliquots at successive time points revealed no fibrils or amorphous precipitates in electron micrographs. The chemical stability of the samples was investigated by reverse-phase HPLC and MALDI-TOF mass spectrometry of successive aliquots. These examinations revealed slow formation of deamidated single-chain insulin derivatives (<ten percent of the starting material), a well-known process is in which Asparagines are converted to Aspartic acid. This is a well-known chemical change that is not believed to alter the conformation or activity of insulin. The receptor-binding activity at 0 and 90 days was equivalent, consistent with the full activity previously established for deamidated insulin derivatives. These results are shown in FIGS. 3A and 3B, which provide a time course of HPLC chromatogram (FIG. 3A) and MALDI-TOF mass spectrum (FIG. 3B) from 0-109 days. At indicated time intervals (0 to 109 days of incubation), aliquots were withdrawn with sterile syringes and applied onto a reverse-phase C8 HPLC column; the protein and its derivatives were eluted with a methanol gradient. The mass of HPLC-separated peaks was determined with MALDI-TOF MS (Perkin-Elmer, Wellesley, Mass.). The difference of 1-2 mass units between the native analogue and the degradation products represents deamidation. *R and *B represent major peak (native analog) and minor degradation product. There was no evidence of chain separation, formation of covalent dimers, disulfide isomers, or other forms of rearrangement.

A synthetic gene was synthesized to direct the expression of the same polypeptide in yeast *Piscia pastoris* and other microorganisms. The sequence of the DNA is:
TTC/GTC/AAC/CAG/CAC/CTC/TGC/GGC/AGC/GAC/ CTC/GTC/GAA/GCA/CTC/TAC/CT C/GTC/TGC/ GGA/GAA/CGA/GGA/TTC/TTC/TAC/ACA/GAC/ CCA/ACA/GGA/GGA/GGA/C CA/CGA/CGA/GGA/ ATA/GTA/GAA/CAA/TGC/TGC/CAC/AGC/ATA/TGT/ AGC/CTC/TA C/CAA/CTA/GAA/AAC/TAC/TGC/ AAC. (SEQ ID NO: 27) Additional synthetic genes were prepared to direct the synthesis of analogues of this polypeptide containing variant amino-acid substitutions at positions A4, A8, B28 and B29; in addition, successive changes in length of the linker peptide were encoded within the variant DNA sequence.

Receptor-Binding Assays. Relative activity is defined as the ratio of analogue to wild-type human insulin required to displace 50 percent of specifically bound $^{125}$I-human insulin. A human placental membrane preparation containing the insulin receptor (IR) was employed as known in the art. Membrane fragments (0.025 mg protein/tube) were incubated with $^{125}$I-labeled insulin (ca. 30,000 cpm) in the presence of selected concentrations of unlabelled analogue for 18 hours at 4° C. in a final volume of 0.25 ml of 0.05 M Tris-HCl and 0.25 percent (w/v) bovine serum albumin at pH 8. Subsequent to incubation, mixtures are diluted with 1 ml of ice-cold buffer and centrifuged (10,000 g) for 5 min at 4° C. The supernatant will then be removed by aspiration, and the membrane pellet counted for radioactivity. Data is corrected for nonspecific binding (amount of radioactivity remaining membrane associated in the presence of 1 μM human insulin. In all assays the percentage of tracer bound in the absence of competing ligand was less than 15% to avoid ligand-depletion artifacts. An additional assay to monitor changes in activity during the course of incubation of the single-chain analogue at 37° C. was performed using a microtiter plate antibody capture as known in the art. Microtiter strip plates (Nunc Maxisorb) were incubated overnight at 4° C. with AU5 IgG (100 μl/well of 40 mg/ml in phosphate-buffered saline). Binding data were analyzed by a two-site sequential model. A corresponding microtiter plate antibody assay using the IGF Type I receptor was employed to assess cross-binding to this homologous receptor.

Figure 4:
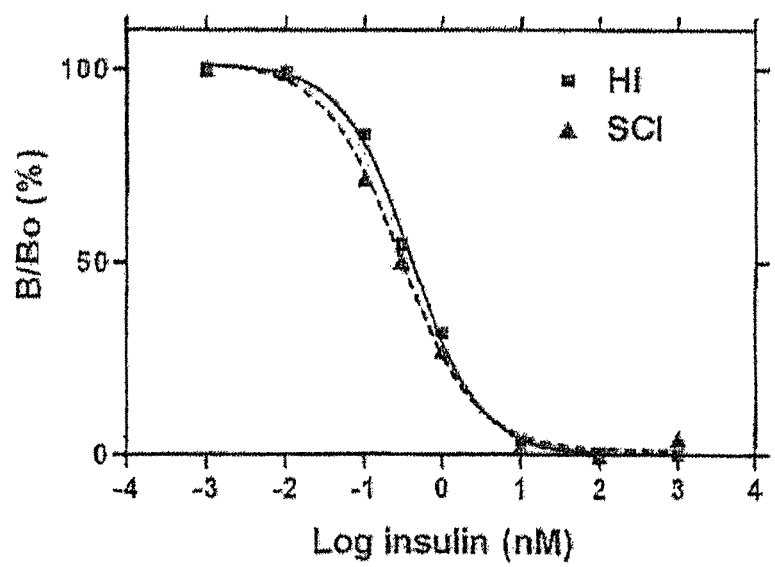

The receptor-binding activity of the 57 mer single-chain insulin analogue (SEQ ID NO: 26) relative to human insulin (SEQ ID NOS: 2 and 3) is 129%+/−8%, as shown in Table I. The affinity of human insulin, whose affinity is 0.05 nM under assay conditions, and that of DKP-insulin, is provided in Table I for comparison purposes. Additionally, FIG. 4 illustrates a receptor-binding assay in which binding of the 57 mer single-chain insulin analogue (SEQ ID NO: 26, dashed line; triangles) was evaluated relative to native human insulin (SEQ ID NOS: 2 and 3, solid line; squares) using human placental membranes containing a mixture of isoforms A and B of the insulin receptor. This assay measures the displacement of receptor-bound $^{125}$I-labeled insulin by either unlabeled analogue or insulin (B/Bo) across a range of unlabeled analog/insulin concentrations. Whereas the activity of miniproinsulin has been previously shown to be reduced by 10.000-fold, the activity of the 57 mer analogue is essentially equivalent to that of wild-type human insulin. Indeed, the slight shift to the left of the displacement curve of the 57 mer analogue indicates a slight increase in biological activity (129±8 percent in four replicates).

TABLE I

Affinity of Insulin and Insulin Analogues to Insulin Receptor

| Sample: | Affinity (relative to human insulin): |
|---|---|
| Human insulin | 100% |
| DKP-insulin | 161 ± 19% |
| 57mer single-chain analogue | 129 ± 8% |
| Corresponding two-chain analogue | 700% |

These data indicate that the affinity of the analogues to the human insulin receptor is as great or greater than that of wild-type human insulin. In addition, it is evident that the linker has reduced the affinity from the super-active range (700%) back to near that of wild-type human insulin (129±8%).

The affinity of the 57 mer single-chain insulin analogue (SEQ ID NO: 26) for the IGF Type I receptor is similar to that of human insulin; the extent of increased affinity, if present, is less than two-fold that of human insulin. This is less than that of lispro-insulin, which has an affinity for IGFR twofold greater than that of insulin.

We have tested the mitogenicity of the 57 mer single-chain insulin analogue (SEQ ID NO: 26) in cell culture and found it to be likewise indistinguishable from human insulin, in each case significantly less mitogenic than IGF-I. To this end, human breast cancer cell line MCF-7 was grown in a humidified atmosphere of 5% $CO_2$-95% air at 37° C. in Eagle's Minimal Essential Medium (MEM, Nacalai Tesque) supplemented with non-essential amino acids, 1% sodium pyruvate, and 2 mM l-glutamine. Growth media were supplemented with 10% fetal bovine serum (FBS) (Invitrogen Life Technologies, Inc., Carlsbad, AA), penicillin (100 U/ml) and streptomycin (100 ug/mL). Approximately $1.0 \times 10^5$ cells were seeded into 35-mm dishes and cultured until subconfluent. Two assays were employed: (i) Cell-growth curves were determined by hemocytometry. Approximately $5 \times 10^4$ were seeded into a 24-well plate and cultured for 24 h. After 24 hour, the medium was removed and replaced with fresh medium containing 0.1% BSA. Twenty-four hours later, various concentrations of insulin, the 57 mer single-chain insulin analogue (SEQ ID NO: 26), the corresponding two-chain analogue lacking the linker (SEQ ID NOS: 28 and 29), or IGF-I were added in fresh medium to the culture medium; the media were changed each day. Cell numbers were determined after 3-days exposure to the hormones. (ii) Cell DNA content was determined using a DNA measurement kit (Invitrogen) following 3-days exposure to the hormones in cell culture as above. As expected, the mitogenicity of the corresponding two-chain analogue lacking the linker (SEQ ID NOS: 28 and 29) was intermediate between the single-chain insulin analogue (SEQ ID NO: 26) (or wild-type insulin) and IGF-I, presumably due to the $Asp^{B10}$ substitution. Thus, the linker allows use of the otherwise favorable $Asp^{B10}$ substitution without incurring enhanced mitogenicity.

The thermodynamic stabilities of the insulin analogues were evaluated by guanidine denaturation (Table II). Data were obtained at 37° C. and neutral pH to correspond to the conditions of an implantable insulin pump or use of an insulin formulation at high temperature. In qualitative accord with past studies at lower temperatures, introduction of $His^{48}$ or $Asp^{B10}$ into a two-chain insulin analogue enhanced thermodynamic stability from 2.4 kcal/mole (wild-type human insulin) to 3.4 kcal/mole ($His^{48}$-insulin) or 3.6 kcal/mole ($Asp^{B10}$-insulin). No change was observed on introduction of $Asp^{B28}$ (2.4 kcal/mole). Simultaneous introduction of four substitutions, $His^{48}$, $Asp^{B10}$ $Asp^{B28}$, and $Pro^{B29}$ ("Corresponding two chain analogue"), also yielded increased stability (3.6 kcal/mole) in a two-chain analogue. A further increase in stability was observed on interposition of the 6-residue linker between B30 and A1 (4.3 kcal/mole) ("57 mer single-chain Analog," SEQ ID NO: 26). Thus, interposition of the linker enables the favorable effects of the substitutions on thermodynamic stability (and hence resistance to chemical degradation) to be retained while at the same time "tuning" the mitogenicity and affinities of the analogue for the insulin receptor and Type I IGF receptor (too high in the single-chain analogue) to ensure their similarity to wild-type human insulin.

TABLE II

Thermodynamic Stabilities of Insulin Analogues (37° C. and pH 7.4)

| Sample | $\Delta G_u$ |
|---|---|
| Insulin | 2.4 kcal/mole |
| $His^{48}$-insulin | 3.4 |
| $Asp^{B10}$-insulin | 3.6 |
| $Asp^{B28}$-insulin | 2.4 |
| 57-mer single-chain Analog | 4.3 |
| Corresponding two-chain analogue | 3.6 |

Figure 5:
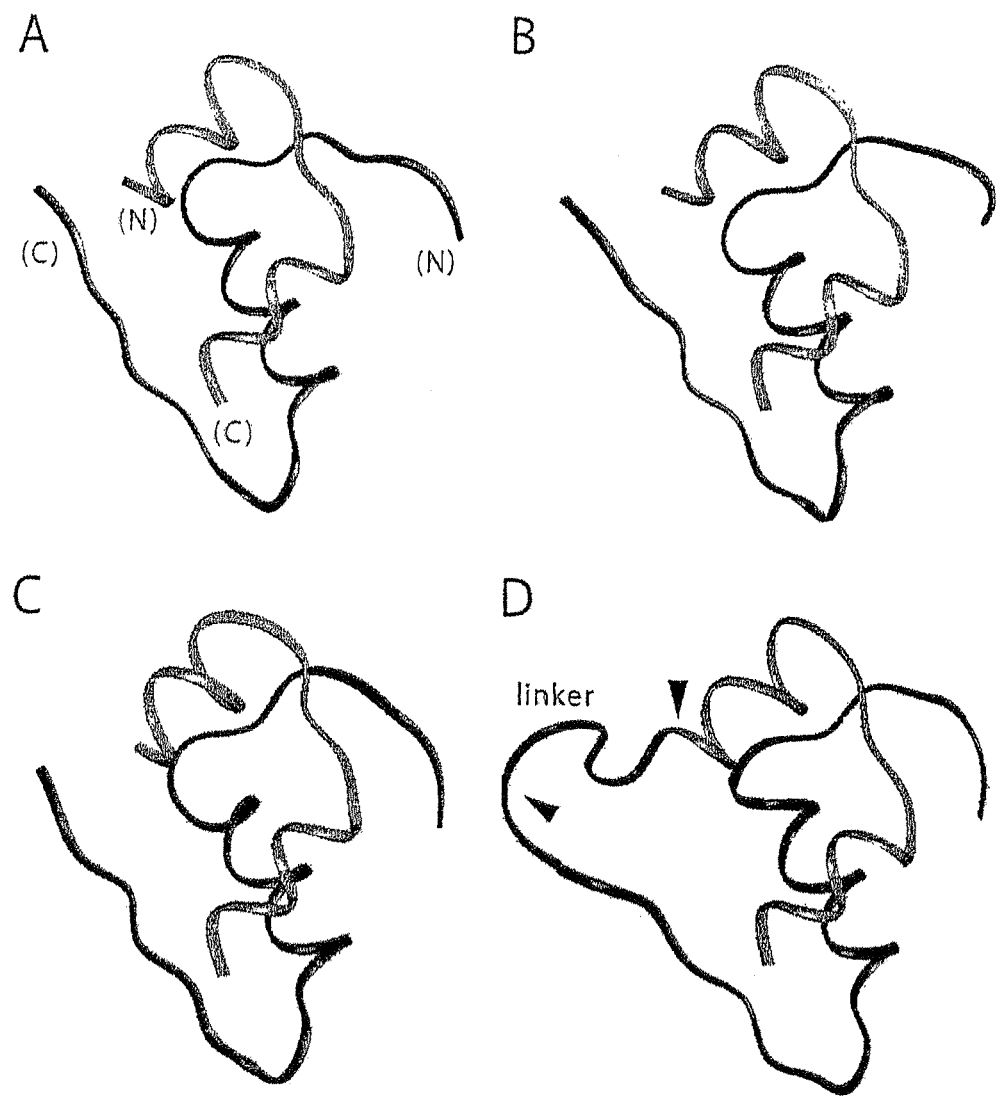

The NMR spectrum of the single-chain analogue exhibits chemical shifts and line widths characteristic of a monodisperse monomeric solution. The solution structure of the analogue is essentially identical to the crystal structure of a 50-mer mini-proinsulin with the exception of the six-residue linker, which in part packs against one face of the hydrophobic core. An NMR structure of the 57 mer is provided in FIG. 5D, which provides the NMR structure of a synthetic 57 mer single-chain insulin analogue (ensemble of DG/RMD structures) in relation to a ribbon model of the crystal structure of mini-proinsulin (a 50mer single-chain analog). The A chain is shown in light gray and B chain in dark gray; the beginning and end of the connecting domain (six residues; GGGPRR) are indicated by arrowheads. 847 restraints were employed in the DG/RMD calculation. Control NMR studies were conducted of the corresponding two-chain insulin analogue containing the same four substitutions ($His^{48}$, $Asp^{B10}$, $Asp^{B28}$, and $Pro^{B29}$). The two-chain insulin is likewise monomeric in neutral solution at a protein concentration near 1 mM. The pattern of chemical shifts is similar to that of the single-chain analogue, indicating a correspondence of structures. Based on DG/RMD calculations, this analogue (FIG. 5C) closely resembles a crystallographic T-state protomer (FIG. 5A) and a previous NMR-derived structure of an engineered insulin monomer (DKP-insulin; FIG. 5B).

Circular Dichroism—Samples were dissolved in either 10 mM phosphate and 100 mM KCl (pH 7.4) or 0.01 N HCl (pH 2.0) at a protein concentration of 25 µM. To remove particulate matter and protein aggregates, samples were filtered (0.22 µM; Satorius, Goetlingen, Germany). Spectra, acquired with an Aviv spectropolarimeter (Aviv Biomedical, Inc., Lakewood, N.J.), were normalized. Data were obtained at 4° C. and fitted by non-linear least squares to a two-state model. CD Spectra for analogues were similar to native and DKP insulins (data not shown).

Fibrillation Assay—Human insulin and analogues were made 60 µM in a deoxygenated buffer consisting of 10 mM sodium phosphate (pH 7.4), and 140 mM NaCl. Samples (in triplicate) were placed in sealed glass vials and placed on an automated tilting table at 37° C. At successive times aliquots were withdrawn and analyzed by a thioflavin T (ThT) fluorescence spectroscopy assay to determine the onset of fibrillation as follows.

Thioflavin T (ThT) was made 1 mM in double-distilled water and stored at 4° C. in the dark. To monitor fibrillation, 10-µl aliquots of samples were obtained at indicated time points and were mixed with 3 ml of ThT assay buffer (5 µM ThT in 50 mM Tris-HCl (pH 7.5) and 100 mM NaCl). Fluorescence measurements were performed using an Aviv spectrofluorometer in 1-cm quartz cuvettes. Emission spectra were collected from 470 to 500 nm following excitation at 450 nm; the integration time was 1 s. ThT in buffer without protein was used as baseline. The fibrillation lag time is defined as the time required to observe twofold enhancement in ThT emission. The threshold of twofold-enhanced ThT fluorescence is followed a rapid increase in turbidity associated with elongation of mature fibrils and a further increase in ThT fluorescence. Under these conditions, human insulin undergoes fibrillation in 3-4 days in the absence of zinc. Lag times prior to fibrillation of the analogues at a protein concentration of 60 μM are provided in Table III. Less than 1% fibrillation has been observed for the 57 mer single-chain insulin analogue after 4 months of incubation at 37° C. Additionally, a similar single chain insulin that is wild type at position B10 (His$^{B10}$) (SEQ ID NO: 31) displays a fibrillation lag time greater than 1 year.

The resistance to fibrillation of a single-chain insulin analogue at a higher concentration has also been examined. The 57 mer single-chain insulin analogue (SEQ ID NO: 26) was incubated at 37° C. at a protein concentration of 3 mM as otherwise described above. A 3 mM concentration is similar to the concentration found in a U-400 formulation of insulin (400 I.U./ml) appropriate for use in an implantable insulin pump. Such a formulation is optimal for an implantable insulin pump to maximize the time between refilling of the insulin reservoir. However, the fibrillation rate of insulin generally increases with insulin concentration. The SCI resists fibrillation under these conditions for greater than 120 days. In comparison, under these conditions and at this concentration, lispro (KP)-insulin forms fibrils in approximately one day.

TABLE III

Fibrillation Lag Times of zinc free-insulin and analogues at 60 μM

| Sample | Lag time (days ± 10%) |
|---|---|
| Insulin | 3.5 |
| KP-insulin | 2.0 |
| DKP-insulin | 11.5 |
| His$^{48}$-insulin | 13 |
| Asp$^{B10}$-insulin | 18 |
| Ala$^{B12}$-DKP-insulin | 40 |
| Trp$^{48}$-KP-insulin | 3 |
| 57-mer single-chain Analog | >120 days |
| Corresponding two-chain analogue | 70 ± 5 days |

Transmission Electron Microscopy—The presence or absence of fibrils (as distinct from amorphous precipitation or crystals) was verified by TEM. Aliquots (10 μl) were deposited on Formvar-coated 400-mesh copper grids (Electron Microscopy Sciences, Hatfield, Pa.) for 5 min. Excess solution was adsorbed to filter paper. Grids were washed three times with distilled water and three times with filtered 1% uranyl acetate for negative staining. Stained grids were allowed to dry for 20 min at room temperature. Specimens were observed with a Jeol 1200EX transmission electron microscope operating with an accelerating voltage of 80 kV.

An additional comparison of a prior single chain insulin analog to current analog was also performed. A single chain insulin analog containing a wild-type insulin A-chain (SEQ ID NO: 2) and a wild-type insulin B-chain (SEQ ID NO: 3) joined by a seven amino acid polypeptide having the sequence of SEQ ID NO: 30 was synthesized as described above. The resulting analog ("Prior SCI") was analyzed using an isoform-specific insulin receptor binding assay as follows. Additionally, a SCI similar to that of the 57-mer single chain analog, with the exception of the position corresponding to the B10 position of insulin being unsubstituted (that is, having histidine at B10) was also synthesized as described above. The resulting polypeptide had the amino acid sequence of SEQ ID NO: 31.

DNA for transfection was prepared according to the method of Mynarcik et al. (J. Biol. Chem., 1997, 272, pp 18650-18655). The receptor cDNAs were expressed transiently in PEAK rapid cells using polyethyleneimine. Cells were harvested by lysis in 0.15M NaCl and 0.1M Tris (pH 8) containing 1% (v/v) Triton X-100 and protease inhibitor cocktail three days post-transfection. Lysates were stored at −80° C. until assay. Receptor-binding assays were performed as described by Mynarcik. Microtiter strip plates (Nunc Maxisorb) were incubated overnight at 4° C. with anti-FLAG IgG (100 ml/well of a 40 mg/ml solution in PBS). Washing, blocking, receptor binding and competitive binding assays with labeled and unlabeled peptides were performed as described. Binding data were analyzed by a two-site sequential model with homologous or heterologous labeled and unlabeled ligands to obtain dissociation constants as described by Whittaker et al. (J. Biol. Chem., 2001, 276, pp 43980-43986).

As shown in Table IV, the receptor binding activity of the analog containing the linker of SEQ ID NO: 30 ("Prior SCI") had greatly reduced affinity for insulin receptors compared to human insulin. In Table IV, the binding affinities for wild type human insulin (HI) and several insulin analogues for the A isoform specific human insulin receptor (HIRA), the B isoform specific human insulin receptor (HIRB), and Insulin-like Growth Factor receptor (IGFR). The insulin analogue indicated as "A8-His, B-10 Asp, B 28-Asp, B 29-Pro ins" is the same as the analogue noted as "corresponding two-chain analogue" in Tables I-III. Single chain insulin analogues (SCI) containing His$^{48}$, Asp$^{B28}$, and Pro$^{B29}$ substitutions with or without an Asp$^{B10}$ substitution were also tested.

The affinities of the insulin analogues to HIRA, HIRB and IGFR are provided as dissociation constants (Kd) and as an absolute number relative to unmodified human insulin. The prior SCI had affinities for HIRA and HIRB of 5 percent and 4 percent of human insulin respectively. Affinity of the prior SCI for IGFR relative to human insulin was greater, but was still only 13 percent of human insulin. The current SCI containing the substitution Asp$^{B10}$ has an affinity for the A isoform insulin receptor approximately 7 fold greater than that of human insulin and an affinity for the B isoform insulin receptor of about half that of human insulin. At the same time, the affinity of this SCI for IFGR is approximately the same as that of human insulin. By way of contrast, the SCI not containing the Asp$^{B10}$ substitution had a reduced affinity for IFGR (0.35 relative to human insulin) but also had lower affinities for HIRA and HIRB compared to the SCI containing the Asp$^{B10}$ substitution (2.0 and 0.36, respectively). The "corresponding two chain analogue," that is, the two chain analogue containing the substitutions Asp$^{B10}$, His$^{48}$, Asp$^{B28}$ and Pro$^{B29}$, had an increased affinity for IFGR (3.54) over that of human insulin as well as increased affinities for HIRA and HIRB (4.25 and 4.7, respectively). The present invention therefore, provides an insulin analogue containing an Asp$^{B10}$ substitution that maintains at least half of the affinity of human insulin for HIRB and has greater affinity for HIRA than human insulin while maintaining the affinity for IFGR at approximately the same level as unmodified human insulin.

TABLE IV

| LIGAND | RECEPTOR | | | | | |
|---|---|---|---|---|---|---|
| | HIRA | | HIRB | | IGFR | |
| | Kd (nM) | Relative Affinity | Kd (nM) | Relative Affinity | Kd (nM) | Relative Affinity |
| HI | 0.034 ± 0.002 | 1 | 0.047 ± 0.003 | 1 | 9.57 ± 0.31 | 1 |
| A8-His, B10-Asp, B28-Asp, B29-Pro ins | 0.008 ± 0.001 | 4.25 | 0.010 ± 0.001 | 4.7 | 2.7 ± 0.003 | 3.54 |
| A8-His, B28-Asp, B29-Pro SCI | 0.017 ± 0.001 | 2.0 | 0.130 ± 0.001 | 0.36 | 27.63 ± 1.18 | 0.35 |
| A8-His, B10-Asp, B28-Asp, B29-Pro SCI | 0.005 ± 0.0003 | 6.8 | 0.093 ± 0.003 | 0.5 | 9.89 ± 0.035 | 0.97 |
| Prior SCI | 0.66 ± 0.08 | 0.05 | 1.28 ± 0.15 | 0.04 | 77.4 ± 15.5 | 0.13 |

Figure 6A:
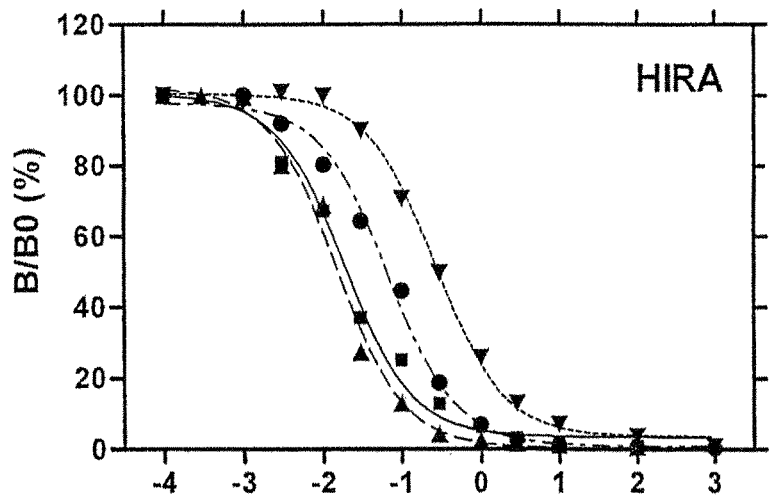
FIG. 6A is a graph of the results of a receptor binding assay in which binding of human insulin and human insulin analogues to human insulin receptor isoform A (HIRA) were evaluated. The displacement of receptor-bound $^{125}$I-labeled insulin by either unlabeled analogue or insulin (B/Bo) is provided across a range of unlabeled analog/insulin concentrations.
Figure 6B:
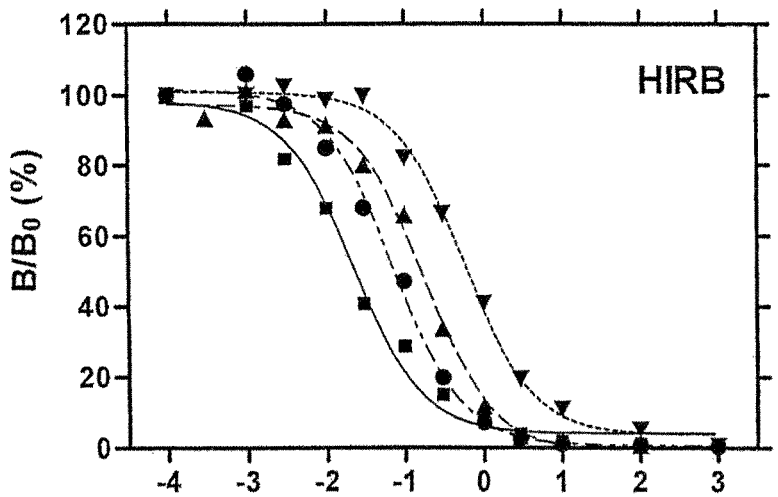
FIG. 6B is a graph of the results of a receptor binding assay in which binding of human insulin and human insulin analogues to human insulin receptor isoform B (HIRB) were evaluated. The displacement of receptor-bound $^{125}$I-labeled insulin by either unlabeled analogue or insulin (B/Bo) is provided across a range of unlabeled analog/insulin concentrations.
Figure 6C:
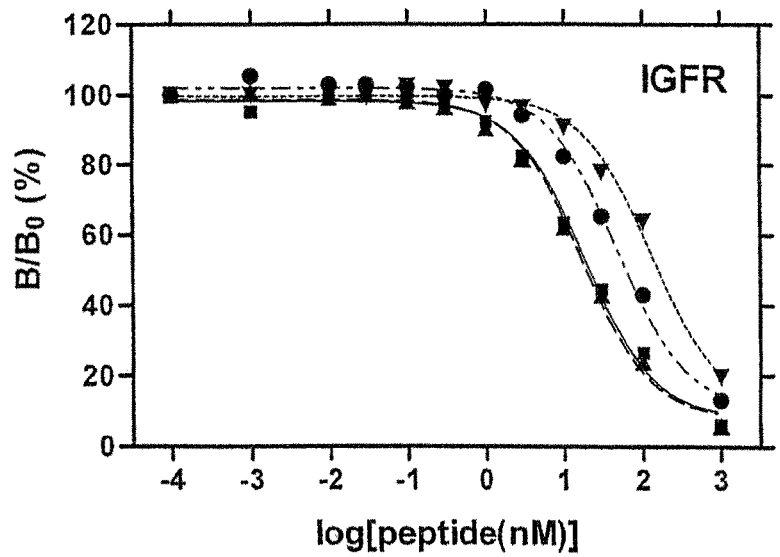
FIG. 6C is a graph of the results of a receptor binding assay in which binding of human insulin and human insulin analogues to Insulin-like Growth Factor Receptor (IGFR) were evaluated. The displacement of receptor-bound $^{125}$I-labeled insulin by either unlabeled analogue or insulin (B/Bo) is provided across a range of unlabeled analog/insulin concentrations.

This is confirmed by the results of the receptor-binding assays shown in FIGS. 6A-6C. The insulin and insulin analogue data are represented as follows: unmodified human insulin (■), single chain insulin (SCI) analogue containing $His^{48}$, $Asp^{B10}$, $Asp^{B28}$, $Pro^{B29}$ substitutions (▲), SCI analogue containing $His^{48}$, $Asp^{B28}$, $Pro^{B29}$ substitutions (●), Prior SCI (▼). In FIG. 6A, the receptor-binding assay utilized HIRA. In FIG. 6B, the receptor binding assay utilized HIRB and in FIG. 6C the receptor-binding assay utilized tested. These assays measure the displacement of receptor-bound $^{125}$I-labeled insulin by either unlabeled analogue or insulin (B/Bo) across a range of unlabeled analog/insulin concentrations.

Table V provides the binding affinities for Insulin-like Growth Factor 1 (IGF-1), wild type human insulin (HI), a single chain insulin (SCI) having the amino acid sequence of SEQ ID NO: 31 ($His^{48}$, $Asp^{B28}$, $Pro^{B29}$), and insulin analogues HUMALOG® ($Lys^{B28}$, $Pro^{B29}$) and LANTUS (having the addition of two arginine residues attached to the carboxy-terminal end of the B-chain). The affinities of these ligands to IGFR are provided as dissociation constants (Kd) and as an absolute number relative to IGF-1. While the SCI of the present invention shows an affinity for IGFR that is less than that of wild type insulin, the analogues HUMALOG® and LANTUS® have affinities approximately 2-3 times that of unmodified human insulin.

TABLE V

| LIGAND | IGFR | |
|---|---|---|
| | Kd (nM) | Relative Affinity |
| IGF-I | 0.047 ± 0.006 | 1 |
| HI | 9.57 ± 0.31 | 0.005 |
| HUMALOG | 5.18 ± 0.18 | 0.009 |
| A8-His, B28-Asp, B29-Pro SCI | 27.63 ± 1.18 | 0.002 |
| LANTUS | 3.14 ± 0.44 | 0.015 |

Figure 7:
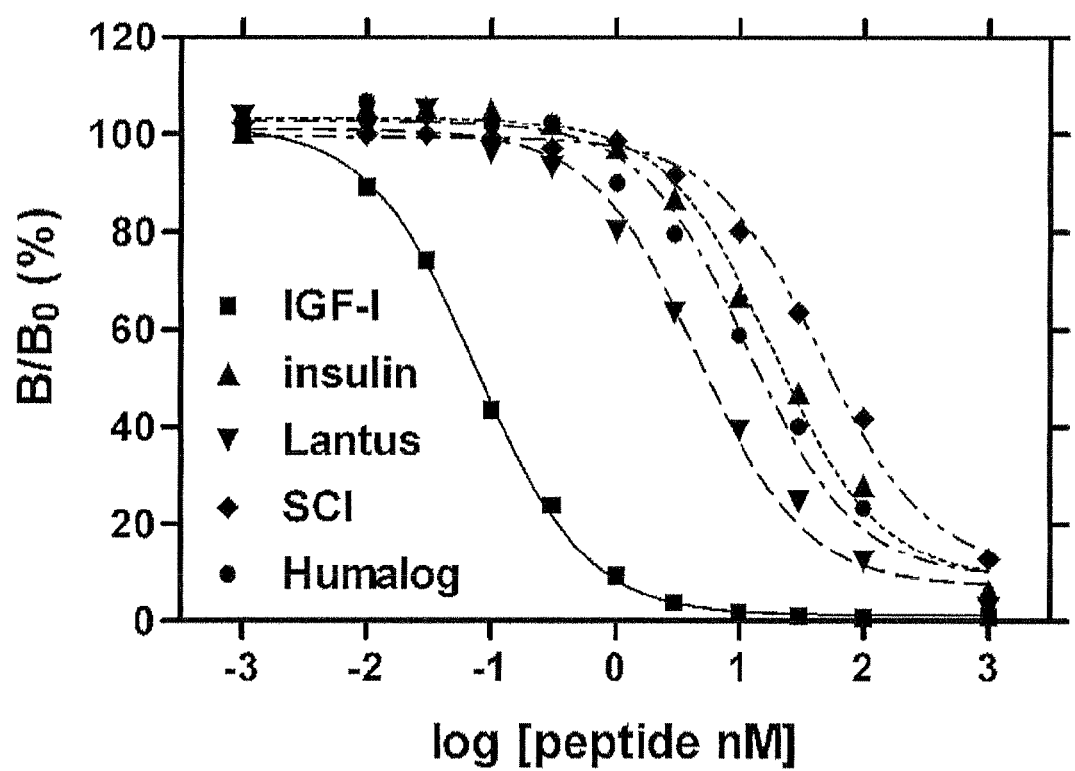
FIG. 7 is a graph of the results of a receptor binding assay comparing the IGFR binding affinity of a single chain insulin (SCI) that is wild type at position B10 (SEQ ID NO: 31), with Insulin-like Growth Factor 1 (IGF-1), wild type human insulin and the insulin analogues sold under the trademarks HUMALOG® and LANTUS®.

This is also reflected in FIG. 7, which is a graph showing the displacement of receptor-bound $^{125}$I-labeled IGF-1 by unlabeled ligand (B/Bo) across a range of unlabeled peptide concentrations.

While not wishing to be bound by theory, the Applicants believe that the reduced binding activity of the prior SCI containing the linker of SEQ ID NO: 30 is due to an altered isoelectric point caused by the presence of lysine and arginine in the linker without an offsetting substitution in the A- or B-chain to retain. The single chain insulin analog of SEQ ID NO: 26, however, has a similar isoelectric point to that of human insulin, as the positive charges provided by the residues introduced in the linker offset at least some of the altered charges introduced by the $Asp^{B10}$, $Asp^{B28}$ and $Pro^{B29}$ substitutions. Additional or alternate substitutions in the A- or B-chains may also be utilized to affect the isoelectric point of a resulting insulin analog. For example, histidine may be maintained at B10 to maintain zinc binding and insulin hexamer formation.

Figure 8:
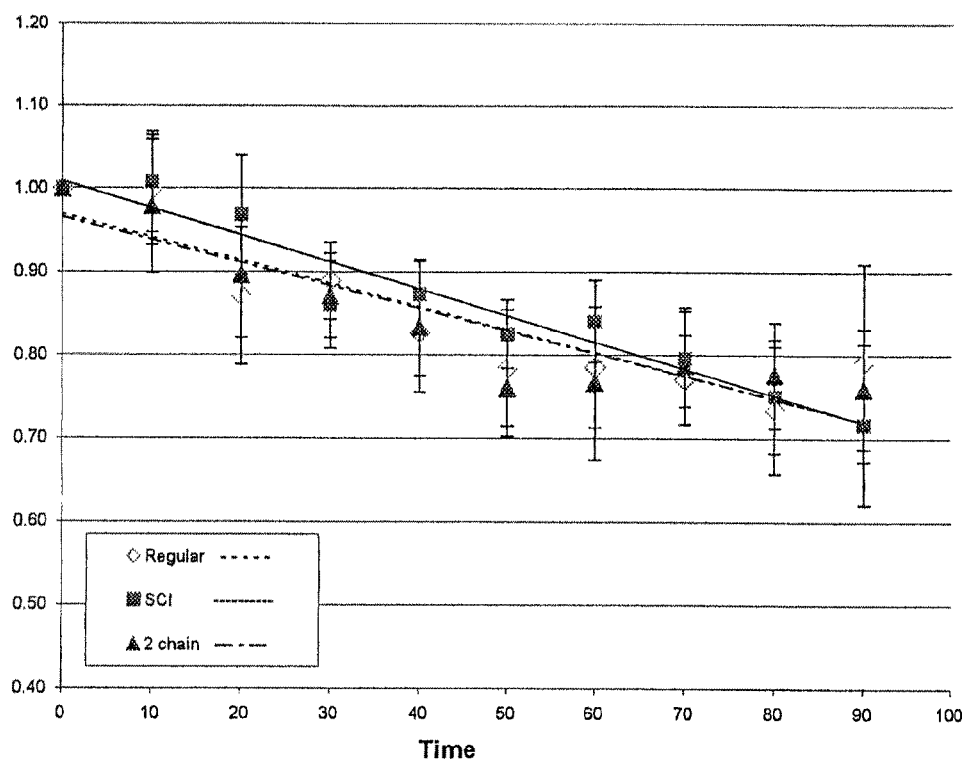
FIG. 8 is a graph showing blood sugar measurements of diabetic Lewis rats over time following injection of human insulin (SEQ ID NOS: 2 and 3), SCI (His$^{48}$, Asp$^{B10}$, Asp$^{B28}$, and Pro$^{B29}$) (SEQ ID NO: 26), or a double stranded analog of the SCI (having the His$^{48}$, Asp$^{B10}$, Asp$^{B28}$, and Pro$^{B29}$ substitutions) (SEQ ID NOS: 28 and 29).

The in vivo potency of the 57 mer SCI containing $His^{48}$, $Asp^{B10}$, $Asp^{B28}$, and $Pro^{B29}$ substitutions (SEQ ID NO: 26) in diabetic rats is equivalent to wild-type human insulin. Male Lewis rats (~250 g body weight) were rendered diabetic with streptozotocin. Human insulin and insulin analogs (SCI (SEQ ID NO: 26) and a two-chain analogue of the SCI lacking the 6-residue linker (SEQ ID NOS: 28 and 29)) were purified by HPLC, dried to powder, and dissolved in insulin diluent (Eli Lilly Corp). Rats were injected subcutaneously at time=0 with 1.5 U/kg body weight in 100 μl of diluent. Blood was obtained from clipped tip of the tail at time 0 and every 10 minutes up to 90 min. Blood glucose was measured using a Hypoguard Advance Micro-Draw meter. Blood glucose concentrations were observed to decrease at rates of 64.2±16.9, 62.0±16.3, and 53.2±11.7 mg/dL per h for human insulin, SCI, and the two-chain control analog, respectively. These values are indistinguishable within variation (FIG. 8). In FIG. 8, the relative blood glucose level over time is shown for human insulin (O), SCI ($His^{48}$, $Asp^{B10}$, $Asp^{B28}$, and $Pro^{B29}$) (■), two chain analogue ($His^{48}$, $Asp^{B10}$, $Asp^{B28}$, and $Pro^{B29}$) (▲). In full dose-response curves, SCI ($His^{48}$, $Asp^{B10}$, $Asp^{B28}$, and $Pro^{B29}$) is likewise indistinguishable in its hypoglycemic action from wild-type human insulin.

Use of $Asp^{B10}$ has previously been avoided in insulin analog formulations in clinical use due to its effect on cross-binding to the IGFR and associated mitogenicity. Testing of $Asp^{B10}$-insulin in Sprague-Dawley rats led to an increased incidence of mammary tumors. IGF-I contains a negative charge at the homologous position (Glu9); it is believed that mimicry of this charge by $Asp^{B10}$ significantly enhances the binding of $Asp^{B10}$ insulin analogs to the IGFR. Surprisingly, we have found that the affinity of SCI ($His^{48}$, $Asp^{B10}$, $Asp^{B28}$, and $Pro^{B29}$) for the IGFR is similar to that of human insulin; any potential increase is <twofold. Since the $Lys^{B28}$-$Pro^{B29}$ substitutions in HUMALOG confer a twofold increase in IGFR cross-binding without a detectable increase in risk of cancer in patients, the IGFR-binding properties of SCI ($His^{48}$, $Asp^{B10}$, $Asp^{B28}$, and $Pro^{B29}$) (SEQ ID NO: 26) are unlikely to be significant.

Based upon the foregoing disclosure, it should now be apparent that the single-chain insulin analogues provided herein will provide increased resistance to fibrillation over natural insulin while maintaining at least the majority of the activity of the insulin. It is, therefore, to be understood that any variations evident fall within the scope of the claimed invention and thus, the selection of specific component elements can be determined without departing from the spirit of the invention herein disclosed and described.

The invention claimed is:

1. An insulin analogue comprising a single chain polypeptide of formula I, $$B\text{-}C\text{-}A \quad (I)$$

wherein B comprises a polypeptide having the sequence:

FVNQHLCGSX$_2$LVEALYLVCGERGFFYTX$_3$ X$_4$T (SEQ ID NO: 33)

where X$_2$ is D or H, X$_3$ is P, D or K, and X$_4$ is K or P, wherein C is a polypeptide selected from the group consisting of:

a polypeptide having the sequence GSEQRR (SEQ ID NO: 21), a polypeptide having the sequence GAGPRR (SEQ ID NO: 24), and a polypeptide having the sequence GPRR (SEQ ID NO: 25), and wherein A comprises a polypeptide having the sequence:

GIVEQCCX$_1$SICSLYQLENYCN (SEQ ID NO: 32)

where X$_1$ is T or H.

2. The insulin analogue of claim 1, wherein A comprises a polypeptide having the sequence GIVEQCCHSICSLYQLENYCN (SEQ ID NO: 29).

3. The insulin analogue of claim 2, wherein $X_3$ is D, and $X_4$ is P.

4. The insulin analogue of claim 3, wherein $X_2$ is D.

5. The insulin analogue of claim 3, wherein $X_2$ is H.

6. The insulin analogue of claim 5, wherein $X_3$ is D, and $X_4$ is P.

7. The insulin analogue of claim 6, wherein $X_2$ is D.

8. The insulin analogue of claim 6, wherein $X_2$ is H.

9. A nucleic acid encoding a polypeptide of formula I, $$B\text{-}C\text{-}A \qquad (I)$$

wherein B comprises a polypeptide having the sequence:

```
                                     (SEQ ID NO: 33)
FVNQHLCGSX2LVEALYLVCGERGFFYTX3 X4T
``` where $X_2$ is D or H, $X_3$ is P, D or K, and $X_4$ is K or P, wherein C is a polypeptide selected from the group consisting of:
- a polypeptide having the sequence GSEQRR (SEQ ID NO: 21),
- a polypeptide having the sequence GAGPRR (SEQ ID NO: 24),
- a polypeptide having the sequence GPRR (SEQ ID NO: 25), and and wherein A comprises a polypeptide having the sequence:

```
                        (SEQ ID NO: 32)
GIVEQCCX1SICSLYQLENYCN
``` where $X_1$ is T or H.

10. An expression vector comprising the nucleic acid according to claim 9.

11. A host cell transformed with the expression vector of claim 10.

12. The nucleic acid of claim 9, wherein A comprises a polypeptide having the sequence GIVEQCCHSICSLYQLENYCN (SEQ ID NO: 29).

13. The nucleic acid of claim 12, wherein $X_3$ is D, and $X_4$ is P.

14. A method of reducing blood glucose levels of a mammal comprising administering a physiologically effective amount of a single chain insulin analogue or a physiologically acceptable salt thereof to a mammal, wherein the single chain insulin analogue comprises a single chain polypeptide of formula I, $$B\text{-}C\text{-}A \qquad (I)$$

wherein B comprises a polypeptide having the sequence:

```
                                     (SEQ ID NO: 33)
FVNQHLCGSX2LVEALYLVCGERGFFYTX3 X4T
``` where $X_2$ is D or H, $X_3$ is P, D or K, and $X_4$ is K or P, wherein C is a polypeptide selected from the group consisting of:

```
                                     (SEQ ID NO: 21)
a polypeptide having the sequence GSEQRR, (SEQ ID NO: 24)
a polypeptide having the sequence GAGPRR,
and (SEQ ID NO: 25)
a polypeptide having the sequence GPRR,
``` and wherein A comprises a polypeptide having the sequence:

```
                       (SEQ ID NO: 32)
GIVEQCCX1SICSLYQLENYCN
``` where $X_1$ is T or H.

15. The method of claim 14, wherein $X_2$ is D.

16. The method of claim 15, wherein the insulin A chain polypeptide comprises a histidine substitution at position A10.

17. The method of claim 16, wherein the mammal is a human.

18. The method of claim 14, wherein the mammal is a human.

* * * * *

SEQUENCE LISTING

<160> NUMBER OF SEQ ID NOS: 33

<210> SEQ ID NO 1
<211> LENGTH: 86
<212> TYPE: PRT
<213> ORGANISM: Homo sapiens

<400> SEQUENCE: 1

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn
                85

<210> SEQ ID NO 2
<211> LENGTH: 21
<212> TYPE: PRT
<213> ORGANISM: Homo sapiens

<400> SEQUENCE: 2

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 3
<211> LENGTH: 30
<212> TYPE: PRT
<213> ORGANISM: Homo sapiens

<400> SEQUENCE: 3

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 4
<211> LENGTH: 61
<212> TYPE: PRT
<213> ORGANISM: Artificial
<220> FEATURE:
<223> OTHER INFORMATION: Artificial single chain insulin
<220> FEATURE:
<221> NAME/KEY: MISC_FEATURE
<222> LOCATION: (31)..(40)
<223> OTHER INFORMATION: Xaa can be of any one of 20 naturally occurring
      amino acids
<220> FEATURE:
<221> NAME/KEY: MISC_FEATURE
<222> LOCATION: (31)..(40)
<223> OTHER INFORMATION: Any 4 or more amino acids can be present

<400> SEQUENCE: 4

Phe Val Asn Gln His Leu Cys Gly Ser His Leu Val Glu Ala Leu Tyr
1               5                   10                  15

```
Leu Val Cys Gly Glu Arg Gly Phe Phe Tyr Thr Pro Lys Thr Xaa Xaa
            20                  25                  30

Xaa Xaa Xaa Xaa Xaa Xaa Xaa Gly Ile Val Glu Gln Cys Cys Thr
        35                  40                  45

Ser Ile Cys Ser Leu Tyr Gln Leu Glu Asn Tyr Cys Asn
    50                  55                  60

<210> SEQ ID NO 5
<211> LENGTH: 61
<212> TYPE: PRT
<213> ORGANISM: Artificial
<220> FEATURE:
<223> OTHER INFORMATION: Artificial single chain insulin
<220> FEATURE:
<221> NAME/KEY: MISC_FEATURE
<222> LOCATION: (32)..(39)
<223> OTHER INFORMATION: Xaa can be any one of 20 naturally occurring
      amino acids
<220> FEATURE:
<221> NAME/KEY: MISC_FEATURE
<222> LOCATION: (32)..(39)
<223> OTHER INFORMATION: Any 2 or more amino acids can be present

<400> SEQUENCE: 5

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Xaa
            20                  25                  30

Xaa Xaa Xaa Xaa Xaa Xaa Xaa Arg Gly Ile Val Glu Gln Cys Cys Thr
        35                  40                  45

Ser Ile Cys Ser Leu Tyr Gln Leu Glu Asn Tyr Cys Asn
    50                  55                  60

<210> SEQ ID NO 6
<211> LENGTH: 61
<212> TYPE: PRT
<213> ORGANISM: Artificial
<220> FEATURE:
<223> OTHER INFORMATION: Artificial single chain insulin
<220> FEATURE:
<221> NAME/KEY: MISC_FEATURE
<222> LOCATION: (33)..(38)
<223> OTHER INFORMATION: Xaa can be 0 or any one of 20 naturallly
      occurring amino acids
<220> FEATURE:
<221> NAME/KEY: MISC_FEATURE
<222> LOCATION: (33)..(38)
<223> OTHER INFORMATION: 0 or any one or more amino acids can be present

<400> SEQUENCE: 6

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Xaa Xaa Xaa Xaa Xaa Xaa Lys Arg Gly Ile Val Glu Gln Cys Cys Thr
        35                  40                  45

Ser Ile Cys Ser Leu Tyr Gln Leu Glu Asn Tyr Cys Asn
    50                  55                  60

<210> SEQ ID NO 7
<211> LENGTH: 61
<212> TYPE: PRT
<213> ORGANISM: Artificial
<220> FEATURE:
<223> OTHER INFORMATION: Artificial single chain insulin
<220> FEATURE:
<221> NAME/KEY: MISC_FEATURE
```

```
<222> LOCATION: (34)..(37)
<223> OTHER INFORMATION: Xaa can be 0 or any one of 20 naturally
      occurring amino acids
<220> FEATURE:
<221> NAME/KEY: MISC_FEATURE
<222> LOCATION: (34)..(37)
<223> OTHER INFORMATION: 0 or any one or more amino acids can be present

<400> SEQUENCE: 7

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Xaa Xaa Xaa Xaa Gln Lys Arg Gly Ile Val Glu Gln Cys Cys Thr
        35                  40                  45

Ser Ile Cys Ser Leu Tyr Gln Leu Glu Asn Tyr Cys Asn
    50                  55                  60

<210> SEQ ID NO 8
<211> LENGTH: 57
<212> TYPE: PRT
<213> ORGANISM: Artificial
<220> FEATURE:
<223> OTHER INFORMATION: Artificial single chain insulin

<400> SEQUENCE: 8

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Gln Lys Arg Gly Ile Val Glu Gln Cys Cys Thr Ser Ile Cys Ser
        35                  40                  45

Leu Tyr Gln Leu Glu Asn Tyr Cys Asn
    50                  55

<210> SEQ ID NO 9
<211> LENGTH: 58
<212> TYPE: PRT
<213> ORGANISM: Artificial
<220> FEATURE:
<223> OTHER INFORMATION: Artificial single chain insulin

<400> SEQUENCE: 9

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Gln Lys Arg Gly Ile Val Glu Gln Cys Cys Thr Ser Ile Cys
        35                  40                  45

Ser Leu Tyr Gln Leu Glu Asn Tyr Cys Asn
    50                  55

<210> SEQ ID NO 10
<211> LENGTH: 58
<212> TYPE: PRT
<213> ORGANISM: Artificial
<220> FEATURE:
<223> OTHER INFORMATION: Artificial single chain insulin

<400> SEQUENCE: 10

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
```

```
            20                  25                  30

Glu Leu Gln Lys Arg Gly Ile Val Glu Gln Cys Cys Thr Ser Ile Cys
        35                  40                  45

Ser Leu Tyr Gln Leu Glu Asn Tyr Cys Asn
    50                  55

<210> SEQ ID NO 11
<211> LENGTH: 59
<212> TYPE: PRT
<213> ORGANISM: Artificial
<220> FEATURE:
<223> OTHER INFORMATION: Artificial single chain insulin

<400> SEQUENCE: 11

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Leu Gln Lys Arg Gly Ile Val Glu Gln Cys Cys Thr Ser Ile
        35                  40                  45

Cys Ser Leu Tyr Gln Leu Glu Asn Tyr Cys Asn
    50                  55

<210> SEQ ID NO 12
<211> LENGTH: 60
<212> TYPE: PRT
<213> ORGANISM: Artificial
<220> FEATURE:
<223> OTHER INFORMATION: Artificial single chain insulin

<400> SEQUENCE: 12

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Leu Gln Lys Arg Gly Ile Val Glu Gln Cys Cys Thr Ser
        35                  40                  45

Ile Cys Ser Leu Tyr Gln Leu Glu Asn Tyr Cys Asn
    50                  55                  60

<210> SEQ ID NO 13
<211> LENGTH: 60
<212> TYPE: PRT
<213> ORGANISM: Artificial
<220> FEATURE:
<223> OTHER INFORMATION: Artificial single chain insulin

<400> SEQUENCE: 13

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Ser Leu Gln Lys Arg Gly Ile Val Glu Gln Cys Cys Thr Ser
        35                  40                  45

Ile Cys Ser Leu Tyr Gln Leu Glu Asn Tyr Cys Asn
    50                  55                  60

<210> SEQ ID NO 14
<211> LENGTH: 61
<212> TYPE: PRT
<213> ORGANISM: Artificial
<220> FEATURE:
```

-continued

<223> OTHER INFORMATION: Artificial single chain insulin

<400> SEQUENCE: 14

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Ser Leu Gln Lys Arg Gly Ile Val Glu Gln Cys Cys Thr
        35                  40                  45

Ser Ile Cys Ser Leu Tyr Gln Leu Glu Asn Tyr Cys Asn
    50                  55                  60

<210> SEQ ID NO 15
<211> LENGTH: 61
<212> TYPE: PRT
<213> ORGANISM: Artificial
<220> FEATURE:
<223> OTHER INFORMATION: Artificial single chain insulin
<220> FEATURE:
<221> NAME/KEY: MISC_FEATURE
<222> LOCATION: (31)..(40)
<223> OTHER INFORMATION: Xaa can be any one of 20 naturally occurring
      amino acids
<220> FEATURE:
<221> NAME/KEY: MISC_FEATURE
<222> LOCATION: (31)..(40)
<223> OTHER INFORMATION: Any 4 or more amino acids may be present

<400> SEQUENCE: 15

Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Thr Xaa Xaa
            20                  25                  30

Xaa Xaa Xaa Xaa Xaa Xaa Xaa Xaa Gly Ile Val Glu Gln Cys Cys Thr
        35                  40                  45

Ser Ile Cys Ser Leu Tyr Gln Leu Glu Asn Tyr Cys Asn
    50                  55                  60

<210> SEQ ID NO 16
<211> LENGTH: 61
<212> TYPE: PRT
<213> ORGANISM: Artificial
<220> FEATURE:
<223> OTHER INFORMATION: Artificial single chain insulin
<220> FEATURE:
<221> NAME/KEY: MISC_FEATURE
<222> LOCATION: (31)..(40)
<223> OTHER INFORMATION: Xaa can be any one of 20 naturally occurring
      amino acids
<220> FEATURE:
<221> NAME/KEY: MISC_FEATURE
<222> LOCATION: (31)..(40)
<223> OTHER INFORMATION: Any 4 or more amino acids can be present

<400> SEQUENCE: 16

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Asp Thr Xaa Xaa
            20                  25                  30

Xaa Xaa Xaa Xaa Xaa Xaa Xaa Xaa Gly Ile Val Glu Gln Cys Cys Thr
        35                  40                  45

Ser Ile Cys Ser Leu Tyr Gln Leu Glu Asn Tyr Cys Asn
    50                  55                  60

<210> SEQ ID NO 17

```
<211> LENGTH: 61
<212> TYPE: PRT
<213> ORGANISM: Artificial
<220> FEATURE:
<223> OTHER INFORMATION: Artificial single chain insulin
<220> FEATURE:
<221> NAME/KEY: MISC_FEATURE
<222> LOCATION: (31)..(40)
<223> OTHER INFORMATION: Xaa can be any one of 20 naturally occurring
      amino acids
<220> FEATURE:
<221> NAME/KEY: MISC_FEATURE
<222> LOCATION: (31)..(40)
<223> OTHER INFORMATION: Any 4 or more amino acids can be present

<400> SEQUENCE: 17

Phe Val Asn Gln His Leu Cys Gly Ser Asp Leu Val Glu Ala Leu Tyr
1               5                   10                  15

Leu Val Cys Gly Glu Arg Gly Phe Phe Tyr Thr Pro Lys Thr Xaa Xaa
            20                  25                  30

Xaa Xaa Xaa Xaa Xaa Xaa Xaa Xaa Gly Ile Val Glu Gln Cys Cys Thr
            35                  40                  45

Ser Ile Cys Ser Leu Tyr Gln Leu Glu Asn Tyr Cys Asn
    50                  55                  60

<210> SEQ ID NO 18
<211> LENGTH: 58
<212> TYPE: PRT
<213> ORGANISM: Artificial
<220> FEATURE:
<223> OTHER INFORMATION: Artificial single chain insulin
<220> FEATURE:
<221> NAME/KEY: MISC_FEATURE
<222> LOCATION: (34)..(34)
<223> OTHER INFORMATION: Xaa can be any one of 20 naturally occurring
      amino acids

<400> SEQUENCE: 18

Phe Val Asn Gln His Leu Cys Gly Ser Asp Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Xaa Gln Lys Arg Gly Ile Val Glu Gln Cys Cys Thr Ser Ile Cys
        35                  40                  45

Ser Leu Tyr Gln Leu Glu Asn Tyr Cys Asn
    50                  55

<210> SEQ ID NO 19
<211> LENGTH: 6
<212> TYPE: PRT
<213> ORGANISM: Artificial
<220> FEATURE:
<223> OTHER INFORMATION: Synthesized construct

<400> SEQUENCE: 19

Gly Gly Gly Pro Arg Arg
1               5

<210> SEQ ID NO 20
<211> LENGTH: 5
<212> TYPE: PRT
<213> ORGANISM: Artificial
<220> FEATURE:
<223> OTHER INFORMATION: Synthesized construct

<400> SEQUENCE: 20

Gly Gly Pro Arg Arg
1               5
```

-continued

```
<210> SEQ ID NO 21
<211> LENGTH: 6
<212> TYPE: PRT
<213> ORGANISM: Artificial
<220> FEATURE:
<223> OTHER INFORMATION: Synthesized construct

<400> SEQUENCE: 21

Gly Ser Glu Gln Arg Arg
1               5

<210> SEQ ID NO 22
<211> LENGTH: 6
<212> TYPE: PRT
<213> ORGANISM: Artificial
<220> FEATURE:
<223> OTHER INFORMATION: Synthesized construct from insulin connecting
      peptide

<400> SEQUENCE: 22

Arg Arg Glu Gln Lys Arg
1               5

<210> SEQ ID NO 23
<211> LENGTH: 8
<212> TYPE: PRT
<213> ORGANISM: Artificial
<220> FEATURE:
<223> OTHER INFORMATION: Synthesized construct from insulin connecting
      peptide

<400> SEQUENCE: 23

Arg Arg Glu Ala Leu Gln Lys Arg
1               5

<210> SEQ ID NO 24
<211> LENGTH: 6
<212> TYPE: PRT
<213> ORGANISM: Artificial
<220> FEATURE:
<223> OTHER INFORMATION: Synthesized construct

<400> SEQUENCE: 24

Gly Ala Gly Pro Arg Arg
1               5

<210> SEQ ID NO 25
<211> LENGTH: 4
<212> TYPE: PRT
<213> ORGANISM: Artificial
<220> FEATURE:
<223> OTHER INFORMATION: Synthesized construct

<400> SEQUENCE: 25

Gly Pro Arg Arg
1

<210> SEQ ID NO 26
<211> LENGTH: 57
<212> TYPE: PRT
<213> ORGANISM: Artificial
<220> FEATURE:
<223> OTHER INFORMATION: Artificial single chain insulin

<400> SEQUENCE: 26

Phe Val Asn Gln His Leu Cys Gly Ser Asp Leu Val Glu Ala Leu Tyr
```

```
                1               5                  10                  15
Leu Val Cys Gly Glu Arg Gly Phe Phe Tyr Thr Asp Pro Thr Gly Gly
                        20                  25                  30

Gly Pro Arg Arg Gly Ile Val Glu Gln Cys Cys His Ser Ile Cys Ser
            35                  40                  45

Leu Tyr Gln Leu Glu Asn Tyr Cys Asn
        50                  55

<210> SEQ ID NO 27
<211> LENGTH: 171
<212> TYPE: DNA
<213> ORGANISM: Artificial
<220> FEATURE:
<223> OTHER INFORMATION: Synthesized construct encoding human insulin
      analogue using condon preferences of Piscia pastoris

<400> SEQUENCE: 27
ttcgtcaacc agcacctctg cggcagcgac ctcgtcgaag cactctacct cgtctgcgga      60
gaacgaggat tcttctacac agacccaaca ggaggaggac cacgacgagg aatagtagaa    120
caatgctgcc acagcatatg tagcctctac caactagaaa actactgcaa c             171

<210> SEQ ID NO 28
<211> LENGTH: 30
<212> TYPE: PRT
<213> ORGANISM: Artificial
<220> FEATURE:
<223> OTHER INFORMATION: Human insulin B-chain peptide analogue

<400> SEQUENCE: 28

Phe Val Asn Gln His Leu Cys Gly Ser Asp Leu Val Glu Ala Leu Tyr
1               5                   10                  15

Leu Val Cys Gly Glu Arg Gly Phe Phe Tyr Thr Asp Pro Thr
            20                  25                  30

<210> SEQ ID NO 29
<211> LENGTH: 21
<212> TYPE: PRT
<213> ORGANISM: Artificial
<220> FEATURE:
<223> OTHER INFORMATION: Human insulin A-chain peptide analogue

<400> SEQUENCE: 29

Gly Ile Val Glu Gln Cys Cys His Ser Ile Cys Ser Leu Tyr Gln Leu
1               5                   10                  15

Glu Asn Tyr Cys Asn
            20

<210> SEQ ID NO 30
<211> LENGTH: 7
<212> TYPE: PRT
<213> ORGANISM: Artificial
<220> FEATURE:
<223> OTHER INFORMATION: Synthesized construct

<400> SEQUENCE: 30

Gly Gly Gly Pro Gly Lys Arg
1               5

<210> SEQ ID NO 31
<211> LENGTH: 57
<212> TYPE: PRT
<213> ORGANISM: Artificial
<220> FEATURE:
<223> OTHER INFORMATION: Artificial single chain insulin
```

```
<400> SEQUENCE: 31

Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Pro Thr Gly Gly
            20                  25                  30

Gly Pro Arg Arg Gly Ile Val Glu Gln Cys Cys His Ser Ile Cys Ser
        35                  40                  45

Leu Tyr Gln Leu Glu Asn Tyr Cys Asn
    50                  55

<210> SEQ ID NO 32
<211> LENGTH: 21
<212> TYPE: PRT
<213> ORGANISM: Artificial
<220> FEATURE:
<223> OTHER INFORMATION: human insulin A-chain or analogue thereof
<220> FEATURE:
<221> NAME/KEY: MISC_FEATURE
<222> LOCATION: (8)..(8)
<223> OTHER INFORMATION: Where Xaa is T or H

<400> SEQUENCE: 32

Gly Ile Val Glu Gln Cys Cys Xaa Ser Ile Cys Ser Leu Tyr Gln Leu
1               5                   10                  15

Glu Asn Tyr Cys Asn
            20

<210> SEQ ID NO 33
<211> LENGTH: 30
<212> TYPE: PRT
<213> ORGANISM: Artificial
<220> FEATURE:
<223> OTHER INFORMATION: human insulin B-chain or analogue thereof
<220> FEATURE:
<221> NAME/KEY: MISC_FEATURE
<222> LOCATION: (10)..(10)
<223> OTHER INFORMATION: Xaa is D or H
<220> FEATURE:
<221> NAME/KEY: MISC_FEATURE
<222> LOCATION: (28)..(28)
<223> OTHER INFORMATION: Xaa is P, D or K
<220> FEATURE:
<221> NAME/KEY: MISC_FEATURE
<222> LOCATION: (29)..(29)
<223> OTHER INFORMATION: Xaa is K, P

<400> SEQUENCE: 33

Phe Val Asn Gln His Leu Cys Gly Ser Xaa Leu Val Glu Ala Leu Tyr
1               5                   10                  15

Leu Val Cys Gly Glu Arg Gly Phe Phe Tyr Thr Xaa Xaa Thr
            20                  25                  30
```